US012708615B2

(12) United States Patent
Fex et al.

(10) Patent No.: US 12,708,615 B2
(45) **Date of Patent: *Aug. 18, 2026**

(54) SELECTIVE ANGIOTENSIN II RECEPTOR LIGANDS

(71) Applicant: Vicore Pharma AB, Stockholm (SE)

(72) Inventors: Tomas Fex, Mölndal (SE); Bengt Ohlsson, Mölndal (SE); Anders Hallberg, Uppsala (SE); Mats Larhed, Uppsala (SE)

(73) Assignee: Vicore Pharma AB, Stockholm (SE)

( * ) Notice: Subject to any disclaimer, the term of this patent is extended or adjusted under 35 U.S.C. 154(b) by 375 days.

This patent is subject to a terminal disclaimer.

(21) Appl. No.: 18/283,484

(22) PCT Filed: Mar. 23, 2022

(86) PCT No.: PCT/GB2022/050727
§ 371 (c)(1),
(2) Date: Sep. 22, 2023

(87) PCT Pub. No.: WO2022/200787
PCT Pub. Date: Sep. 29, 2022

(65) Prior Publication Data

US 2024/0197685 A1 Jun. 20, 2024

(30) Foreign Application Priority Data

Mar. 23, 2021 (GB) .................................... 2104033

(51) Int. Cl.

| | |
|---|---|
| ***A61K 31/4178*** | (2006.01) |
| ***A61K 31/4439*** | (2006.01) |
| ***C07D 409/10*** | (2006.01) |
| ***C07D 409/14*** | (2006.01) |

(52) U.S. Cl.
CPC ...... *A61K 31/4178* (2013.01); *A61K 31/4439* (2013.01); *C07D 409/10* (2013.01); *C07D 409/14* (2013.01)

(58) Field of Classification Search
CPC ............ A61K 31/4178; A61K 31/4439; C07D 409/10; C07D 409/14; A61P 9/00; A61P 11/00; A61P 13/02; A61P 37/00
USPC .......................................................... 514/341
See application file for complete search history.

(56) References Cited

U.S. PATENT DOCUMENTS

| | | | |
|---|---|---|---|
| 5,468,764 A | 11/1995 | Heitsch et al. | |
| 5,482,957 A | 1/1996 | Wagner et al. | |
| 5,604,251 A | 2/1997 | Heitsch et al. | |
| 5,807,878 A | 9/1998 | Corbier et al. | |
| 5,811,445 A | 9/1998 | Corbier et al. | |
| 2004/0167176 A1 | 8/2004 | Alterman et al. | |
| 2012/0035232 A1 | 2/2012 | Steckelings et al. | |
| 2024/0174657 A1* | 5/2024 | Fex ........................ | A61P 11/00 |

FOREIGN PATENT DOCUMENTS

| | | |
|---|---|---|
| JP | 2004-533457 A | 11/2004 |
| WO | 1994/28896 A1 | 12/1994 |
| WO | 1999/43339 A1 | 9/1999 |
| WO | 2002/096883 A1 | 12/2002 |
| WO | 2003/064414 A1 | 8/2003 |
| WO | 2004/046141 A1 | 6/2004 |
| WO | 2016/092329 A1 | 6/2016 |
| WO | 2016/107879 A2 | 7/2016 |
| WO | 2016/139475 A1 | 9/2016 |
| WO | 2017/221012 A1 | 12/2017 |

(Continued)

OTHER PUBLICATIONS

De Gasparo et al., International union of pharmacology. XXIII. The angiotensin II receptors. Pharmacol Rev. Sep. 2000;52(3):415-72.
King et al., Idiopathic pulmonary fibrosis. Lancet. Dec. 3, 2011;378(9807):1949-61.
Ley et al., Clinical course and prediction of survival in idiopathic pulmonary fibrosis. Am J Respir Crit Care Med. Feb. 15, 2011;183(4):431-40.
Mahalingam et al., Selective angiotensin II AT(2) receptor agonists with reduced CYP 450 inhibition. Bioorg Med Chem. Jun. 15, 2010;18(12):4570-90.
Noble et al., Pulmonary fibrosis: patterns and perpetrators. J Clin Invest. Aug. 2012;122(8):2756-62.

(Continued)

*Primary Examiner* — Taylor V Oh
(74) *Attorney, Agent, or Firm* — McCarter & English, LLP; Michael J. DeGrazia; Sujatha Rochford

(57) ABSTRACT

There is provided pharmaceutical compounds of formula (I), wherein $R^1$, $R^2$, $R^3$, $R^4$, $R^5$, $R^6$, $Y^1$, $Y^2$, $Y^3$ and $Y^4$ have meanings given in the description, which compounds are useful in the treatment of autoimmune and/or fibrotic diseases, including interstitial lung diseases, such as idiopathic pulmonary fibrosis and sarcoidosis.

(I)

20 Claims, No Drawings

(56) References Cited

FOREIGN PATENT DOCUMENTS

| | | | |
|---|---|---|---|
| WO | 2019/008393 | A1 | 1/2019 |
| WO | 2021/053344 | A1 | 3/2021 |
| WO | 2021/186185 | A1 | 9/2021 |
| WO | 2022/049372 | A1 | 3/2022 |

OTHER PUBLICATIONS

Rafii et al., A review of current and novel therapies for idiopathic pulmonary fibrosis. J Thorac Dis. Feb. 2013;5(1):48-73.

Gopalan et al., Angiotensin II AT2 receptor ligands with phenylthiazole scaffolds. Bioorg Med Chem. Jul. 1, 2022;65:116790, 12 pages.

Wan et al., Design, synthesis, and biological evaluation of the first selective nonpeptide AT2 receptor agonist. J Med Chem. Nov. 18, 2004;47(24):5995-6008.

Wannberg et al., A convenient transesterification method for synthesis of AT2 receptor ligands with improved stability in human liver microsomes. Bioorg Med Chem Lett. Feb. 1, 2018;28(3):519-522.

International Search Report and Written Opinion for Application No. PCT/GB2022/050727, dated Jun. 23, 2022, 12 pages.

* cited by examiner

SELECTIVE ANGIOTENSIN II RECEPTOR LIGANDS

CROSS REFERENCE TO RELATED APPLICATIONS

This application is a 35 U.S.C. § 371 national stage filing of International Application No. PCT/GB2022/050727, filed on Mar. 23, 2022, which claims the benefit of GB Patent Application No. 2104033.2, filed Mar. 23, 2021, the entire contents of each of which are incorporated herein by reference.

FIELD OF THE INVENTION

This invention relates to novel pharmaceutically-useful compounds, in particular compounds that are angiotensin II (Ang II) agonists, more particularly agonists of the Ang II type 2 receptor (hereinafter the AT2 receptor), and especially agonists that bind selectively to that receptor. The invention further relates to the use of such compounds as medicaments, to pharmaceutical compositions containing them, and to synthetic routes to their production.

BACKGROUND OF THE INVENTION

Renin, a protease, cleaves its only known substrate (angiotensinogen) to form angiotensin I (Ang I), which in turn serves as a substrate to angiotensin converting enzyme (ACE) to form Ang II. The endogenous hormone Ang II is a linear octapeptide ($Asp^1$-$Arg^2$-$Val^3$-$Tyr^4$-$Ile^5$-$His^6$-$Pro^7$-$Phe^8$), and is an active component of the renin angiotensin system (RAS). The angiotensin II type 1 (AT1) receptor is expressed in most organs, and is believed to be responsible for the majority of the pathological effects of Ang II.

Several studies in adult individuals appear to demonstrate that, in the modulation of the response following Ang II receptor stimulation, activation of the AT2 receptor has opposing effects to those mediated by the AT1 receptor. The AT2 receptor has also been shown to be involved in apoptosis and inhibition of cell proliferation (de Gasparo M et al., *Pharmacol. Rev.* (2000), 52, 415-472). More recently, AT2 receptor agonists have been shown to be of potential utility in the treatment and/or prophylaxis of disorders of the alimentary tract, such as dyspepsia and irritable bowel syndrome, as well as multiple organ failure (see international patent application WO 99/43339). The expected pharmacological effects of agonism of the AT2 receptor are described in general in de Gasparo M et al., vide supra.

The stimulating effects of Ang II on vascular tone, cell growth, inflammation and extracellular matrix synthesis are mainly coupled to the AT1 receptor in any organ, whereas the function of the AT2 receptor seems to be more prevalent in damaged tissue and exerts reparative properties and properties opposing the AT1 receptor. For example, the AT2 receptor has been shown to be of importance in relation to reduction of myocyte hypertrophy and fibrosis.

Interstitial lung diseases (ILDs) are a group of lung diseases that affect the interstitium, characterised by tissue around alveoli becoming scarred and/or thickened, and so inhibiting the respiratory process.

ILDs are distinct from obstructive airway diseases (e.g. chronic obstructive airway disease (COPD) and asthma), which are typically characterized by narrowing (obstruction) of bronchi and/or bronchioles. ILDs may be caused by injury to the lungs, which triggers an abnormal healing response but, in some cases, these diseases have no known cause.

ILDs can be triggered by chemicals (silicosis, asbestosis, certain drugs), infection (e.g. pneumonia) or other diseases (e.g. rheumatoid arthritis, systemic sclerosis, myositis or systemic lupus erythematosus).

The most common ILDs are idiopathic pulmonary fibrosis (IPF) and sarcoidosis, both of which are characterised by chronic inflammation and reduced lung function.

Sarcoidosis is a disease of unknown cause that is characterised by collections of inflammatory cells that form lumps (granulomas), often beginning in the lungs (as well as the skin and/or lymph nodes, although any organ can be affected). When sarcoidosis affects the lungs, symptoms include coughing, wheezing, shortness of breath, and/or chest pain.

Treatments for sarcoidosis are patient-specific. In most cases, symptomatic treatment with non-steroidal anti-inflammatory drugs (NSAIDs) is possible, but for those presenting lung symptoms, glucocorticoids (e.g. prednisone or prednisolone), antimetabolites and/or monoclonal anti-tumor necrosis factor antibodies are often employed.

IPF is a lung-disease of unknown cause that affects about 5 million people globally. It has no curative treatment options except, in rare cases, lung transplantation, resulting in a chronic, irreversible, progressive deterioration in lung function and, in most cases, leading to death within 2-5 years (median survival 2.5 to 3.5 years). While the overall prognosis is poor in IPF, it is difficult to predict the rate of progression in individual patients. Risk factors for IPF include age, male gender, genetic predisposition and history of cigarette smoking. The annual incidence is between 5-16 per 100,000 individuals, with a prevalence of 13-20 cases per 100,000 people, increasing dramatically with age (King Jr T E et al., *Lancet* (2011); 378, 1949-1961; Noble P W et al., *J. Clin. Invest.* (2012); 122, 2756-2762). IPF is limited to the lungs and is recalcitrant to therapies that target the immune system which distinguishes it from pulmonary fibrosis associated with systemic diseases.

Patients with IPF usually seek medical assistance due to chronic and progressive exertional dyspnea and cough. Imaging of the lung classically reveals traction bronchiectasis, thickened interlobar septae and subpleural honeycombing. When all three manifestations are present and there is no evidence of a systemic connective tissue disease or environmental exposure, a diagnosis of IPF is very likely. A definite diagnosis is usually made by lung biopsy and requires a multidisciplinary team of expertise including pulmonologists, radiologists and pathologists experienced in interstitial lung diseases.

IPF demonstrates different phenotypes with different prognosis, defined as mild, moderate and severe. Mild cases follow a stable or slow progressive path with patients sometimes taking several years to seek medical advice. Accelerated IPF has a much more rapid progression with shortened survival, affecting a sub-group of patients, usually male cigarette smokers. Acute exacerbations of IPF are defined as a rapid worsening of the disease, and patients in this sub-population have very poor outcomes with a high mortality rate in the short run. The cause of IPF is unknown but it appears to be a disorder likely arising from an interplay of environmental and genetic factors resulting in fibroblast driven unrelenting tissue remodeling rather than normal repair; a pathogenesis primarily driven by fibrosis rather than inflammation. A growing body of evidence suggests that the disease is initiated through alveolar epithelial cell microinjuries and apoptosis, activating neighboring epithelial cells and attracting stem or progenitor cells that produce the factors responsible for the expansion of the fibroblast and myofibroblast populations in a tumor like way. The fibroblastic foci secrete exaggerated amounts of extracellular matrix that destroys the lung parenchyma and ultimately leads to loss of lung function.

The mean annual rate of decline in lung function (vital capacity) is within a range of 0.13-0.21 litres. Symptoms precede diagnosis by 1-2 years and radiographic signs may precede symptoms (Ley B et al., *Am. J. Respir. Crit. Care Med*. (2011); 183, 431-440).

Numerous treatment approaches have been tested in pre-clinical models and clinical trials such as anti-inflammatory, immune-modulatory, cytotoxic, general anti-fibrotic, anti-oxidant, anti-coagulant, anti-chemokine, anti-angiogenic drugs as well as RAS-blockers, endothelin antagonists, and sildenafil, all of which have basically been shown to provide limited or no benefits (Rafii R et al., *J. Thorac. Dis*. (2013); 5, 48-73).

Current treatment of IPF includes oxygen supplementation. Medications that are used include pirfenidone or nintedanib, but only with limited success in slowing the progression of the disease. Further, both of these drugs commonly cause (predominantly gastrointestinal) side-effects.

There are drawbacks associated with all of the aforementioned ILD (and IPF) drug treatments and there is a real clinical need for safer and/or more effective treatments.

To restore the alveolar epithelium is very desirable as a therapeutic effect in IPF, and therefore stem cell therapy has also been tested. Some preclinical studies have shown promise in the use of pluripotent stem cells that can differentiate into lung epithelial and endothelial cells, thereby repairing lung injury and fibrosis.

Currently, a lung transplant is the only intervention that substantially improves survival in IPF patients. However, complications such as infections and transplant rejection are not uncommon.

The development of new treatment strategies for IPF is therefore important. Thus, the fundamental challenge for the future is to develop appropriate therapeutic approaches that will reverse or stop the progression of the disease.

US patent application US 2004/0167176 describes the preparation of tricyclic heterocycles useful as Ang II receptor agonists.

Selective AT2 receptor agonists with reduced CYP 450 inhibition are described in Mahalingam et al., *Bioorg. Med. Chem*. (2010); 18, 4570-4590.

Transesterification methods for synthesis of AT2 receptor ligands with improved stability in human liver microsomes are described in Wannberg et al., *Bioorg. Med. Chem. Lett*. (2018); 28, 519-522.

In particular, international patent application WO 2002/096883 describes the preparation of imidazolyl, triazolyl, and tetrazolyl thiophene sulfonamides and derivatives as AT2 receptor agonists. Of the compounds described in that document (as Example 1) is the compound C21 (N-butyloxycarbonyl-3-(4-imidazol-1 -ylmethylphenyl)-5-isobutylthiophene-2-sulfon-amide). C21 was selected for clinical development from a group of about 20 related analogues as a selective AT2 receptor agonist. It is now in clinical development for treatment of AT2 receptor related disorders, including IPF (see, for example, international patent application WO 2016/139475).

C21 has also been indicated to be of potential use in the treatment of inter alia, stroke, spinal cord injury, sickle cell disease, muscular dystrophy, cancer treatment-related cardiotoxicity, peripheral neuropathy and systemic sclerosis (see, for example, international patent applications WO 2004/046141, WO 2016/092329, WO 2016/107879, WO 2016/139475, WO 2017/221012, WO 2019/008393, and US patent application US 2012/035232).

It has been found during development that C21 has the disadvantage that it is both a potent inhibitor of several Cytochrome P450 enzymes (CYPs), especially CYP 2C9 and CYP 3A4, potentially affecting the metabolism of other drugs, and also rapidly hydrolysed to an inactive sulfonamide metabolite. It is thus a fundamental challenge to develop potent and selective AT2 agonists that are stable metabolically and/or exhibit less inhibition of CYP enzymes.

We have found, surprisingly, that certain chemically-modified compounds as defined hereinafter are not only selective AT2 receptor agonists but are also more potent, have a significantly improved stability to metabolic hydrolysis and/or exhibit less inhibition of CYP enzymes, compared to C21.

DESCRIPTION OF THE INVENTION

In a first aspect of the invention, there is provided a compound of formula I,

I

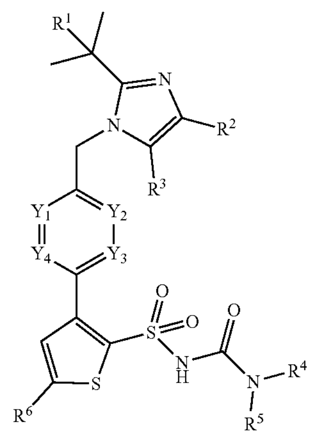

wherein:

- $R^1$ represents $C_{1-2}$alkyl (optionally substituted by one or more fluorine atoms), $OR^7$, or a fluorine atom;
- $R^2$ and $R^3$ each independently represent H or $C_{1-6}$ alkyl, optionally substituted by one or more halogen atoms;
- $Y^1$, $Y^2$, $Y^3$ and $Y^4$ independently represent —CH—, —CF— or —N—;
- $R^4$ represents $C_{1-6}$ alkyl, $C_{1-6}$ alkoxy, $C_{1-6}$ alkoxy-$C_{1-6}$ alkyl, the alkyl parts of each of which are optionally substituted by one or more halogen atoms, or
- $R^4$ represents aryl, $C_{1-6}$ alkylaryl, $C_{1-3}$ alkenylaryl, heteroaryl, $C_{1-6}$ alkylheteroaryl or $C_{1-3}$ alkenylheteroaryl, each of which are optionally substituted by one or more substituents selected from halogen, —$CF_3$, $CF_3O$—, $C_{1-6}$ alkyl, and $C_{1-6}$ alkoxy;
- $R^5$ represents H or $C_{1-6}$ alkyl, each of which is optionally substituted by one or more halogen atoms;
- $R^6$ represents $C_{2-4}$ alkyl, optionally substituted by one or more halogen atoms; and
- $R^7$ represents H or methyl, optionally substituted by one or more fluorine atoms, or a pharmaceutically-acceptable salt thereof, which compounds and salts are referred to together hereinafter as "the compounds of the invention".

For purposes of interpreting this specification, the following definitions will apply and whenever appropriate, terms used in the singular will also include the plural and vice versa.

Compounds may be named according to IUPAC nomenclature generated by the program Chemdoodle 8.1.0.

For the avoidance of doubt, the skilled person will understand that references herein to compounds of particular aspects of the invention (such as any aspect of the invention referring to compounds of formula I as defined hereinbefore) will include references to all embodiments and particular features thereof, which embodiments and particular features may be taken in combination to form further embodiments and features of the invention.

Unless indicated otherwise, all technical and scientific terms used herein have the same meaning as those commonly understood by one of ordinary skill in the art to which this invention pertains.

Pharmaceutically acceptable salts include acid addition salts and base addition salts. Such salts may be formed by conventional means, for example by reaction of a free acid or a free base form of a compound of the invention with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared using techniques known to those skilled in the art, such as by exchanging a counter-ion of a compound of the invention in the form of a salt with another counter-ion, for example using a suitable ion exchange resin.

Particular acid addition salts that may be mentioned include carboxylate salts such as formate, acetate, trifluoroacetate, benzoate, oxalate, fumarate, maleate and the like, sulfonate salts such as methanesulfonate, ethanesulfonate, toluenesulfonate and the like, halide salts such as hydrochloride, hydrobromide and the like, sulfate and phosphate salts such as sulfate or phosphate and the like.

Particular base addition salts that may be mentioned include salts formed with alkali metals (such as Li, Na and K salts), alkaline earth metals (such as Mg and Ca salts), or other metals (such as Al and Zn salts), and amine bases (such as ammonia, ethylenediamine, ethanolamine, diethanolamine, triethanolamine, tromethamine). More particularly, base addition salts that may be mentioned include Mg, Ca and, most particularly, K and Na salts.

Compounds of the invention may exist as solids, and thus the scope of the invention includes all amorphous, crystalline and part crystalline forms thereof, and may also exist as oils. Where compounds of formula I exist in crystalline and part crystalline forms, such forms may include solvates, which are included in the scope of the invention.

Compounds of the invention may also exist in solution (i.e. in solution in a suitable solvent). For example, compounds of formula I may exist in aqueous solution, in which case compounds of the invention may exist in the form of hydrates.

Compounds of the invention may contain double bonds and, unless otherwise indicated, may thus exist as E (entgegen) and Z (zusammen) geometric isomers about each individual double bond. Unless otherwise specified, all such isomers and mixtures thereof are included within the scope of the invention.

Compounds of the invention may also exhibit tautomerism. All tautomeric forms and mixtures thereof are included within the scope of the invention (particularly those of sufficient stability to allow for isolation thereof).

Compounds of the invention may also contain one or more asymmetric carbon atoms and may therefore exhibit optical and/or diastereoisomerism (i.e. existing in enantiomeric or diastereomeric forms). Diastereoisomers may be separated using conventional techniques, e.g. chromatography or fractional crystallisation. The various stereoisomers (i.e. enantiomers) may be isolated by separation of a racemic or other mixture of the compounds using conventional, e.g. fractional crystallisation or HPLC, techniques. Alternatively the desired enantiomer or diastereoisomer may be obtained from appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution; for example, with a homochiral acid followed by separation of the diastereomeric derivatives by conventional means such as chromatography), or by reaction with an appropriate chiral reagent or chiral catalyst, all of which methods and processes may be performed under conditions known to the skilled person. Unless otherwise specified, all stereoisomers and mixtures thereof are included within the scope of the invention.

As used herein, the term "halogen", when used herein, includes fluorine (F), chlorine (C), bromine (Br) and iodine (I). Likewise, the term "halo", if and when used herein, includes fluoro, chloro, bromo and iodo.

Unless otherwise specified, $C_{1-6}$ alkyl groups (e.g. $C_{1-2}$ alkyl groups), $C_{2-4}$ alkyl groups and the alkyl parts of $C_{1-6}$ alkoxy, $C_{1-6}$ alkoxy-$C_{1-6}$ alkyl, $C_{1-6}$ alkylaryl, $C_{1-3}$ alkenylaryl, $C_{1-6}$ alkylheteroaryl and $C_{1-3}$ alkenylheteroaryl groups, defined herein may be straight-chain or, when there is a sufficient number (i.e. a minimum of two or three, as appropriate) of carbon atoms, be branched-chain, and/or cyclic (e.g. forming a $C_{3-6}$ cycloalkyl group). When there is a sufficient number (i.e. a minimum of four) of carbon atoms, such groups may also be part-cyclic (e.g. forming a $C_{4-6}$ partial cycloalkyl group). For example, cycloalkyl groups that may be mentioned include cyclopropyl, cyclobutyl, cyclopentyl and cyclohexyl. Similarly, part-cyclic alkyl groups (which may also be referred to as "part-cycloalkyl" groups) that may be mentioned include cyclopropylmethyl. When there is a sufficient number of carbon atoms, such groups may also be multicyclic (e.g. bicyclic or tricyclic) and/or spirocyclic.

Alkyl groups and alkoxy groups may, when there is a sufficient number (i.e. a minimum of three) of carbon atoms, be unsaturated and thus incorporate a double bond or triple bond.

Particular alkyl groups that may be mentioned include straight chain (i.e. not branched and/or cyclic) alkyl groups. For example, $C_{1-6}$ alkyl groups and the alkyl parts of $C_{1-6}$ alkoxy groups, include but are not limited to n-butyl, sec-butyl, isobutyl, tert-butyl; propyl, such as n-propyl, 2-methylpropyl or isopropyl; ethyl; and methyl.

For the avoidance of any doubt, the point of attachment of the $C_{1-6}$ alkyl groups and the alkyl parts of $C_{1-6}$ alkoxy-$C_{1-6}$ alkyl, $C_{1-6}$ alkylaryl, $C_{1-3}$ alkenylaryl, $C_{1-6}$ alkylheteroaryl and $C_{1-3}$ alkenylheteroaryl groups, is via the alkyl part of such groups.

For the avoidance of doubt, alkoxy groups are attached to the rest of the molecule via the oxygen atom in that group and alkoxyalkyl groups are attached to the rest of the molecule via the alkyl part of that group.

Unless otherwise specified, alkoxy refers to an O-alkyl group in which the term "alkyl" has the meaning(s) given above.

As used herein, references to heteroatoms will take their normal meaning as understood by one skilled in the art. Particular heteroatoms that may be mentioned include phosphorus, selenium, silicon, boron, oxygen, nitrogen and sulfur (e.g. oxygen, nitrogen and sulfur, such as oxygen and nitrogen).

As may be used herein, references to "heteroaryl" (which may also be referred to as heteroaromatic) rings or groups may refer to heteroaromatic groups containing one or more heteroatoms (such as one or more heteroatoms selected from oxygen, nitrogen and/or sulfur). Such heteroaryl groups may comprise one, two, or three rings, of which at least one is aromatic (which aromatic ring(s) may or may not contain the one or more heteroatom). Substituents on heteroaryl/heteroaromatic groups may, where appropriate, be located on any suitable atom in the ring system, including a heteroatom (e.g. on a suitable N atom).

The point of attachment of heteroaryl/heteroaromatic groups may be via any atom in the ring system including (where appropriate) a heteroatom. Bicyclic heteroaryl/heteroaromatic groups may comprise a benzene ring fused to one or more further aromatic or non-aromatic heterocyclic rings, in which instances, the point of attachment of the polycyclic heteroaryl/heteroaromatic group may be via any ring including the benzene ring or the heteroaryl/heteroaromatic or heterocyclyl ring.

For the avoidance of doubt, the skilled person will understand that heteroaryl groups that may form part of compounds of the invention are those that are chemically obtainable, as known to those skilled in the art. Various heteroaryl groups will be well-known to those skilled in the art, such as pyridinyl, pyrrolyl, furanyl, thiophenyl, oxadiazolyl, thiadiazolyl, thiazolyl, oxazolyl, pyrazolyl, triazolyl, tetrazolyl, isoxazolyl, isothiazolyl, imidazolyl, imidazopyrimidinyl, imidazothiazolyl, thienothiophenyl, pyrimidinyl, furopyridinyl, indolyl, azaindolyl, pyrazinyl, pyrazolopyrimidinyl, indazolyl, pyrimidinyl, quinolinyl, isoquinolinyl, quinazolinyl, benzofuranyl, benzothiophenyl, benzoimidazolyl, benzoxazolyl, benzothiazolyl, benzotriazolyl and purinyl.

For the avoidance of doubt, the oxides of heteroaryl/heteroaromatic groups are also embraced within the scope of the invention (e.g. the N-oxide).

As stated above, heteroaryl includes polycyclic (e.g. bicyclic) groups in which one ring is aromatic (and the other may or may not be aromatic). Hence, other heteroaryl groups that may be mentioned include groups such as benzo[1,3]dioxolyl, benzo[1,4]dioxinyl, dihydrobenzo[d]isothiazole, 3,4-dihydrobenz[1,4]oxazinyl, dihydrobenzothiophenyl, indolinyl, 5H,6H,7H-pyrrolo[1,2-b]pyrimidinyl, 1,2,3,4-tetrahydroquinolinyl, thiochromanyl and the like.

As may be used herein, the term aryl may refer to $C_{6-14}$ (e.g. $C_{6-10}$) aromatic groups. Such groups may be monocyclic or bicyclic and, when bicyclic, be either wholly or partly aromatic. $C_{6-10}$ aryl groups that may be mentioned include phenyl, naphthyl, 1,2,3,4-tetrahydronaphthyl, indanyl, and the like (e.g. phenyl, naphthyl, and the like).

Aromatic groups may be depicted as cyclic groups comprising therein a suitable number of double bonds to allow for aromaticity.

The skilled person will understand that aryl groups that may form part of compounds of the invention are those that are chemically obtainable, as known to those skilled in the art.

For the avoidance of doubt, the point of attachment of substituents on aryl groups may be via any suitable carbon atom of the ring system.

The present invention also embraces isotopically-labelled compounds of the present invention which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Hence, the compounds of the invention also include deuterated compounds, i.e. compounds of the invention in which one or more hydrogen atoms are replaced by the hydrogen isotope deuterium.

In cases in which the identity of two or more substituents in a compound of the invention may be the same, the actual identities of the respective substituents are not in any way interdependent. For example, in the situation in which two or more halo groups are present, those groups may be the same or different (e.g. two chloro groups or a fluoro and a chloro group). Similarly, where two or more alkyl groups are present, the groups in question may be the same or different in terms of their number of carbon atoms and/or whether they are linear, branched, unsaturated or otherwise.

Further, when it is specified that a substituent is itself optionally substituted by one or more substituents (e.g. butyl optionally substituted by one or more groups independently selected from halo), these substituents where possible may be positioned on the same or different atoms. Such optional substituents may be present in any suitable number thereof (e.g. the relevant group may be substituted with one or more such substituents, such as one such substituent).

Where groups are referred to herein as being optionally substituted it is specifically contemplated that such optional substituents may be not present (i.e. references to such optional substituents may be removed), in which case the optionally substituted group may be referred to as being unsubstituted.

Unless otherwise specified, substituents (whether optional or otherwise) may be located at any point on a group to which they may be attached. In this respect, alkyl and alkoxy groups (for example) that may be substituted by one or more substituents may also be terminated by such substituents (by which we mean located at the terminus of an e.g. alkyl or alkoxy chain).

For the avoidance of doubt, in cases in which the identity of two or more substituents in a compound of formula I may be the same, the actual identities of the respective substituents are not in any way interdependent. For example, in the situation in which $R^2$ and $R^3$ are both $C_{1-6}$ alkyl, the $C_{1-6}$ alkyl groups in question may be the same or different.

The skilled person will appreciate that compounds of the invention that are the subject of this invention include those that are obtainable, i.e. those that may be prepared in a stable form. That is, compounds of the invention include those that are sufficiently robust to survive isolation, e.g. from a reaction mixture, to a useful degree of purity.

Preferred compounds of the invention include those in which:

- when $R^1$ represents a methyl or an ethyl group, it is optionally substituted by up to three fluorine atoms (e.g. $CH_2CF_3$);
- $R^2$ and $R^3$ independently represent H or a $C_{1-4}$ alkyl group (such as methyl, ethyl, propyl (e.g. n-propyl) or butyl (e.g. n-butyl)), optionally substituted by up to three halogen atoms (e.g. $CH_2CHClCH_2CH_2F$ or $CH_2CF_3$);

$Y^1$ represents —CH—, —CF— or —N—;

$Y^2$ represents —CH— or —CF—

$Y^3$ represents —CH—;

$Y^4$ represents —CH— or —N—;

$R^4$ represents a $C_{1-4}$ alkyl group (such as ethyl, propyl (e.g. n-propyl or isopropyl), or butyl (e.g. tert-butyl, isobutyl or n-butyl)), $C_{1-4}$ alkoxy-$C_{1-4}$-alkyl (such as methoxyethyl), phenyl, $C_{1-3}$ alkylaryl or $C_{1-3}$ alkylheteroaryl, each of which are optionally substituted or terminated by up to three halogen atoms (such as F);

$R^5$ represents H or $C_{1-4}$ alkyl group (such as methyl, ethyl, propyl (e.g. n-propyl) or butyl (e.g. isobutyl));

$R^6$ represents ethyl, propyl (e.g. n-propyl) or butyl (e.g. n-butyl), optionally substituted by one or more halogens.

More preferred compounds of the invention include those in which:

$R^1$ represents methyl, $OR^7$ or a fluorine atom;

$R^2$ and $R^3$ independently represent H or methyl;

$Y^1$, $Y^2$, $Y^3$ and $Y^4$ independently represent —CH— or —CF—;

$R^5$ represents H, methyl, ethyl, n-propyl, n-butyl or isobutyl;

$R^6$ represents n-propyl, n-butyl or isobutyl, optionally substituted or more preferably terminated by up to three fluorine atoms;

$R^7$ represents H or methyl.

Particularly preferred compounds of the invention include those in which:

$R^1$ represents methyl;

$R^2$ and $R^3$ both represent H;

$Y^1$ represents —CH— or —CF—;

$Y^2$, $Y^3$ and $Y^4$ all represent —CH—;

$R^4$ represents ethyl, n-propyl or n-butyl, optionally terminated by up to three fluorine atoms; methoxyethyl; benzyl; 2-methylfuryl, 2-methylthiophenyl or 2-methylpyridyl;

$R^5$ represents H;

$R^6$ represents isobutyl.

Thus, preferred compounds of the invention that may be mentioned include:

furan-2-ylmethyl-3-[[5-isobutyl-3-[4-[(2-tert-butyl-imidazol-1-yl)methyl]phenyl]-2-thienyl]sulfonyl]urea, thiophen-2-ylmethyl-3-[[5-isobutyl-3-[4-[(2-tert-butyl-imidazol-1-yl)methyl]phenyl]-2-thienyl] sulfonylurea, 2-methoxyethyl-3-[[5-isobutyl-3-[4-[(2-tert-butyl-imidazol-1-yl)methyl]phenyl]-2-thienyl]sulfonylureas, pyridin-2-ylmethyl-3-[[5-isobutyl-3-[4-[(2-tert-butyl-imidazol-1-yl)methyl]phenyl]-2-thienyl]sulfonylureas, 1-[[3-[4-[(2-tert-butylimidazol-1-yl)methyl]-3-fluoro-phenyl]-5-isobutyl-2-thienyl]sulfonyl]-3-(2-pyridylmethyl) urea, 1-[[3-[4-[(2-tert-butylimidazol-1-yl)methyl]-3-fluoro-phenyl]-5-isobutyl-2-thienyl]sulfonyl]-3-ethyl-urea, or 1-[[3-[4-[(2-tert-butylimidazol-1-yl)methyl]-3-fluoro-phenyl]-5-isobutyl-2-thienyl]sulfonyl]-3-(2-thienylmethyl) urea.

IUPAC names may be generated from the program Chemdoodle 8.1.0.

More preferred compounds of the invention include the compounds of the examples described hereinafter.

Compounds of formula I may be made in accordance with techniques well known to those skilled in the art, for example as described hereinafter.

According to a further aspect of the invention there is provided a process for the preparation of a compound of formula I, which process comprises:

(i) Reaction of a compound of formula II,

II

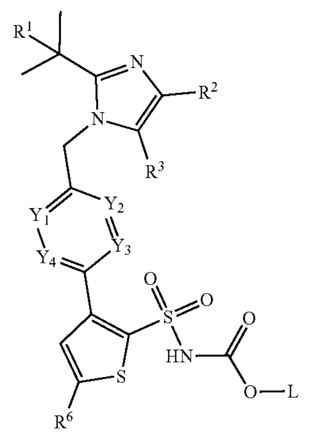

wherein, $R^1$, $R^2$, $R^3$, $R^6$, $Y^1$, $Y^2$, $Y^3$ and $Y^4$ are as hereinbefore defined and L represents $C_{1-6}$ alkyl or an aryl group (such as phenyl) with a compound of formula III, or a salt thereof,

III

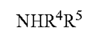

wherein $R^4$ and $R^5$ are as hereinbefore defined, for example at around room temperature or above (e.g. up to 70-110° C.) in the presence of a suitable solvent, such as toluene, acetonitrile or dioxane and/or a suitable base, such as triethylamine or 4-dimethylaminopyridine or potassium carbonate.

(ii) In the case of compounds of formula I in which $R^5$ represents H, reaction of a compound of formula IV,

IV

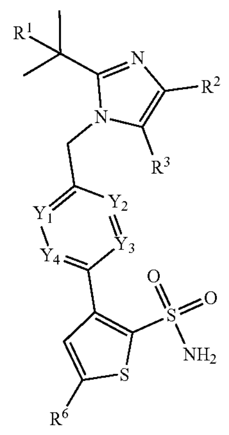

wherein $R^1$, $R^2$, $R^3$, $R^6$, $Y^1$, $Y^2$, $Y^3$ and $Y^4$ are as hereinbefore defined with a compound of formula V,

V

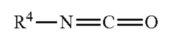

wherein $R^4$ is as hereinbefore defined, for example at around room temperature or above (e.g. up to 60-70°

C.), optionally in the presence of copper (I) chloride or boron trifluoride etherate and/or a suitable base (e.g. pyrollidinopyridine, pyridine, triethylamine, tributylamine, trimethylamine, dimethylaminopyridine, di-isopropylamine, 1,8-diazabicyclo[5.4.0]undec-7-ene, or mixtures thereof) and an appropriate solvent (e.g. pyridine, dichloromethane, ethyl acetate, tetrahydrofuran, dimethylformamide, acetonitrile, or mixtures thereof).

(iii) In the case of compounds of formula I in which $R^5$ represents H, reaction of a compound of formula IV as hereinbefore defined with a formula VI,

VI

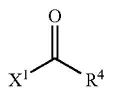

wherein $R^4$ is as hereinbefore defined and $X^1$ is a suitable leaving group (e.g. halo (e.g. chloro or bromo), —O—$C_{1-6}$ alkyl or —O—$C_{1-6}$ aryl (e.g. —OPh), for example under microwave irradiation at above room temperature in the presence of a suitable base (e.g. sodium hydrogen carbonate, pyrollidinopyridine, pyridine, triethylamine, tributylamine, trimethylamine, dimethylaminopyridine, di-isopropylamine, 1,8-diazabicyclo[5.4.0]undec-7-ene, or mixtures thereof) and an appropriate solvent (e.g. acetonitrile, pyridine, dichloromethane, chloroform, tetrahydrofuran, dimethylformamide, or toluene).

Compounds of formula II may be prepared by reaction of a compound of formula IV as hereinbefore defined with a compound of formula VII,

VII

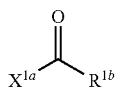

wherein $X^{1a}$ and $X^{1b}$ each represent $X^1$ as hereinbefore defined and may be the same or different, for example at under, around or above room temperature (e.g. 0° C., or up to 50-70° C.) in the presence of a suitable base as hereinbefore defined and an appropriate solvent (e.g. pyridine, dichloromethane, chloroform, tetrahydrofuran, dimethylformamide, acetonitrile or toluene).

Compounds of formula IV may be prepared by reaction of a compound of formula VIII,

VIII

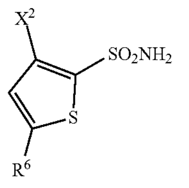

wherein $R^6$ is as hereinbefore defined, or a N-protected derivative thereof, and $X^2$ represents a suitable cross-coupling group, with a compound of formula IX,

IX

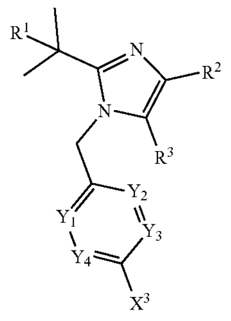

wherein $R^1$, $R^2$, $R^3$, $Y^1$, $Y^2$, $Y^3$, and $Y^4$ are as hereinbefore defined and $X^3$ represents a suitable cross-coupling group. The above coupling reaction is preferably a Suzuki reaction, and therefore may be performed under standard Suzuki conditions, which means that one of $X^2$ and $X^3$ represents either one of the suitable Suzuki cross-coupling groups (or 'partners'), i.e. boronic acid (—$B(OH)_2$) or a boronic acid ester (e.g. MIDA derivative or a pinacol ester) and halo groups, such as iodo or bromo and the other represents the other group. The standard Suzuki conditions may be applied in this reaction, which includes, for example, the presence of an appropriate coupling catalyst system (e.g. a palladium catalyst, such as [1,1'-bis(diphenylphosphine)ferrocene]-dichloropalladium(II), [1,1'-bis(diphenylphosphine)ferrocene]-dichloropalladium(II) complex with dichloromethane, $Pd(PPh_3)_4$ or $Pd(OAc)_2$/ligand (wherein the ligand may be, for example, $PPh_3$, $P(o\text{-}Tol)_3$ or 1,1'-bis(diphenylphosphino)ferrocene)) and a suitable base (e.g. sodium hydroxide, sodium carbonate, potassium carbonate, caesium carbonate, triethylamine or di-iso-propylamine), as well as a suitable solvent system (e.g. toluene, ethanol, n-butanol, dimethoxymethane, dimethylformamide, ethylene glycol dimethyl ether, water, dioxane or mixtures thereof). This reaction may be carried out at above room temperature (e.g. at the reflux temperature of the solvent system that is employed). This reaction may be carried out under microwave irradiation at above room temperature. If a protected version of a compound of formula VIII is employed, this reaction may be followed by deprotection of the $SO_2NH$— group under standard conditions, for example as described hereinafter. The reaction of a compound of formula VIII with a compound of formula IX may also be followed by reaction of the intermediate so formed with a suitable acid to form an acid addition salt or, more preferably, a N-protected version thereof. Suitable acid addition salts include fumarate, trifluoroacetate and oxalate salts.

Compounds of formula IV may alternatively be prepared by reaction of a compound of formula X,

X

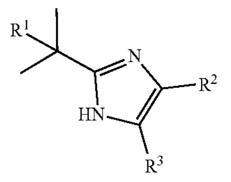

wherein $R^1$, $R^2$ and $R^3$ are as hereinbefore defined with a compound of formula XI,

XI

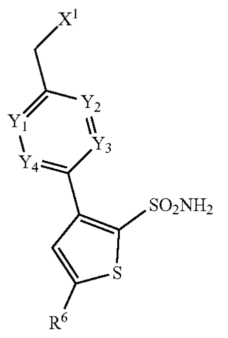

wherein $R^6$, $X^1$, $Y^1$, $Y^2$, $Y^3$ and $Y^4$ are as hereinbefore defined ($X^1$, in particular, may represent bromo), or a N-protected derivative thereof, for example at around or below room temperature in the presence of a suitable base (e.g. pyridine) and an appropriate organic solvent (e.g. toluene). If a protected version of a compound of formula XI is employed, this reaction may be followed by deprotection of the $SO_2NH$-group under standard conditions, for example as described hereinafter. Additionally, compounds of formula IV may be prepared in this way for example according, or analogously, to processes described in inter alia UK patent application GB 2281298.

Compounds of formula IX may be prepared by standard techniques, for example by way of reaction of a compound of formula X as hereinbefore defined with a compound of formula XII,

XII

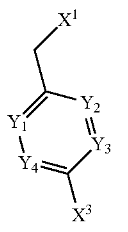

wherein $X^1$, $X^3$, $Y^1$, $Y^2$, $Y^3$ and $Y^4$ are as hereinbefore defined, for example under similar conditions to those described hereinbefore in respect of preparation of compounds of formula IV.

Compounds of formula XI are known in the art. For example, they may be prepared according, or analogously, to processes described in inter alia U.S. Pat. No. 5,312,820, UK patent application GB 2281298, and/or international patent application WO 02/096883.

Compounds of formula VIII are known in the art. For example, they may be prepared according, or analogously, to processes described in inter alia international patent application WO 02/096883.

Compounds of formulae III, V, VI, VII, X and XII are either commercially available, are known in the literature, or may be obtained either by analogy with the processes described herein, or by conventional synthetic procedures, in accordance with standard techniques, from readily-available starting materials using appropriate reagents and reaction conditions.

It will be appreciated by those skilled in the art that, in the processes described above and hereinafter, the functional groups of intermediate compounds may need to be protected by protecting groups.

Functional groups that are desirable to protect include sulphonamido, amido, amino and aldehyde. Suitable protecting groups for sulphonamido, amido and amino include tert-butyloxycarbonyl, benzyloxycarbonyl, 2-trimethylsilylethoxycarbonyl (Teoc) or tert-butyl. Suitable protecting groups for aldehyde include alcohols, such as methanol or ethanol, and diols, such as 1,3-propanediol or, preferably, 1,2-ethanediol (so forming a cyclic acetal). The protection and deprotection of functional groups may take place before or after a reaction in the above-mentioned schemes.

Protecting groups may be applied and removed in accordance with techniques that are well-known to those skilled in the art and as described hereinafter. For example, protected compounds/intermediates described herein may be converted chemically to unprotected compounds using standard deprotection techniques. The type of chemistry involved will dictate the need, and type, of protecting groups as well as the sequence for accomplishing the synthesis. The use of protecting groups is fully described in "*Protective Groups in Organic Synthesis"*, 3rd edition, T. W. Greene & P. G. M. Wutz, Wiley-Interscience (1999), the contents of which are incorporated herein by reference.

Medical and Pharmaceutical Uses

As described herein, the compounds of the invention, and therefore compositions and kits comprising the same, are useful because they possess pharmacological activity, and/or are metabolised in the body following oral or parenteral administration to form compounds that possess pharmacological activity.

Thus, according to a further aspect of the invention, there is provided the compound of the invention, as hereinbefore defined, for use as a pharmaceutical (or for use in medicine).

In particular, compounds of the invention are agonists of AT2 receptors. Compounds of the invention are thus expected to be useful in those conditions in which endogenous production of Ang II is deficient and/or where an increase in the activity of AT2 receptors is desired or required.

More particularly, compounds of the invention are agonists of the AT2 receptor, and, especially, are selective (vs. the AT1 receptor) agonists of that sub-receptor, for example as may be demonstrated in the tests described below.

AT2 receptor agonists include those that fully, and those that partially, activate the AT2 receptor. Compounds of the invention may thus bind selectively to the AT2 receptor, and exhibit agonist activity at the AT2 receptor. By compounds that "bind selectively" to the AT2 receptor, we include that the affinity ratio for the relevant compound (AT2:AT1) at a given concentration is at least 50:1, such as at least 100:1, preferably at least 1000:1.

The compounds of the invention are further expected to be useful in those conditions where AT2 receptors are expressed and their stimulation is desired or required.

In this respect, compounds of the invention are indicated in the treatment of conditions characterised by vasoconstriction, fibrosis, increased cell growth and/or differentiation, increased cardiac contractility, increased cardiovascular hypertrophy, and/or increased fluid and electrolyte retention, as well as skin disorders and musculoskeletal disorders.

Compounds of the invention may also exhibit thromboxane receptor activity. In this respect, compounds of the invention may have an inhibitory effect on platelet activation and/or aggregation (and thus e.g. an antithrombotic effect), and/or may reduce vasoconstriction and/or bronchoconstriction in a therapeutic manner.

Compounds of the invention are further indicated in the treatment of stress-related disorders, and/or in the improvement of microcirculation and/or mucosa-protective mechanisms.

Thus, compounds of the invention are expected to be useful in the treatment of disorders, which may be characterised as indicated above, and which are of, for example, the gastrointestinal tract, the cardiovascular system, the respiratory tract, the kidneys, the eyes, the female reproductive (ovulation) system and the central nervous system (CNS).

Disorders of the gastrointestinal tract that may be mentioned include oesophagitis, Barrett's oesophagus, gastric ulcers, duodenal ulcers, dyspepsia (including non-ulcer dyspepsia), gastro-oesophageal reflux, irritable bowel syndrome (IBS), inflammatory bowel disease (IBD), pancreatitis, hepatic disorders (such as hepatitis), gall bladder disease, multiple organ failure (MOF) and sepsis. Other gastrointestinal disorders that may be mentioned include xerostomia, gastritis, gastroparesis, hyperacidity, disorders of the bilary tract, coelicia, Crohn's disease, ulcerative colitis, diarrhoea, constipation, colic, dysphagia, vomiting, nausea, indigestion and Sjögren's syndrome.

Disorders of the respiratory tract that may be mentioned include inflammatory disorders, such as asthma, obstructive lung diseases (such as chronic obstructive lung disease), pneumonitis, pulmonary hypertension, and adult respiratory distress syndrome.

Disorders of the kidneys that may be mentioned include renal failure, nephritis and renal hypertension.

Disorders of the eyes that may be mentioned include diabetic retinopathy, premature retinopathy and retinal microvascularisation.

Disorders of the female reproductive system that may be mentioned include ovulatory dysfunction.

Cardiovascular disorders that may be mentioned include hypertension, cardiac hypertrophy, cardiac failure (including heart failure with preserved ejection fraction), artherosclerosis, arterial thrombosis, venous thrombosis, endothelial dysfunction, endothelial lesions, post-balloon dilatation stenosis, angiogenesis, diabetic complications, microvascular dysfunction, angina, cardiac arrhythmias, claudicatio intermittens, preeclampsia, myocardial infarction, reinfarction, ischaemic lesions, erectile dysfunction and neointima proliferation.

Disorders of the CNS that may be mentioned include cognitive dysfunctions, dysfunctions of food intake (hunger/satiety) and thirst, stroke, cerebral bleeding, cerebral embolus and cerebral infarction, multiple sclerosis (MS), Alzheimer's disease and Parkinson's disease.

Compounds of the invention may also be useful in the modulation of growth metabolism and proliferation, for example in the treatment of ageing, hypertrophic disorders, prostate hyperplasia, autoimmune disorders (e.g. arthritis, such as rheumatoid arthritis, or systemic lupus erythematosus), psoriasis, obesity, neuronal regeneration, the healing of ulcers, inhibition of adipose tissue hyperplasia, stem cell differentiation and proliferation, fibrotic disorders, cancer (e.g. in, or of, the gastrointestinal tract (including the oesophagus or the stomach), the prostate, the breast, the liver, the kidneys, as well as lymphatic cancer, lung cancer, ovarian cancer, pancreatic cancer, hematologic malignancies, etc), apoptosis, tumours (generally) and hypertrophy, diabetes, neuronal lesions and organ rejection.

Compounds of the invention are also useful in the treatment of stroke, spinal cord injury, sickle cell disease, muscular dystrophy, cancer treatment-related cardiotoxicity, peripheral neuropathy and, in particular, systemic sclerosis.

Compounds of the invention are particularly indicated in the treatment and/or prevention of ILDs, such as sarcoidosis or fibrosis, more specifically pulmonary fibrosis and particularly IPF, as well as conditions that may trigger ILDs, such as systemic sclerosis, rheumatoid arthritis, myositis or systemic lupus erythematosus, or are otherwise associated with ILDs, such as pulmonary hypertension and/or pulmonary arterial hypertension.

Compounds of the invention are particularly useful in the treatment of pulmonary fibrosis, in particular IPF.

According to a further aspect of the present invention, there is provided a method of treatment of pulmonary fibrosis, and in particular IPF), which method comprises administration of a therapeutically effective amount of a compound of the invention to a person suffering from such a condition.

In the treatment of pulmonary fibrosis, including IPF, compounds of the invention may have an anti-fibrotic effect, with reduction of fibrosis and prevention of further deposition of extracellular matrix. Compounds of the invention may reduce lung scarring/wound healing and also have an anti-apoptotic effect, thereby preventing apoptosis of alveolar endothelial cells, being an initiating factor for the development of pulmonary fibrosis. Compounds of the invention may also have an anti-proliferative effect, thus reducing the cancer-like proliferation of fibroblasts and myofibroblasts in pulmonary fibrosis. Compounds of the invention may also improve vascular remodelling in pulmonary fibrosis, thereby reducing secondary pulmonary hypertension. Finally, compounds of the invention may demonstrate anti-inflammatory, anti-growth factor (e.g. transforming growth factor beta) and/or anti-cytokine effects.

In addition, compounds of the invention may also be useful in the treatment or prevention of any fibrotic condition of one or more internal organs characterised by the excessive accumulation of fibrous connective tissue, and/or in the treatment or prevention of fibrogenesis and the morbidity and mortality that may be associated therewith. Such fibrosis may be associated with an acute inflammatory condition, such as acute respiratory distress syndrome (ARDS), severe acute respiratory syndrome (SARS), and multiple-organ inflammation, injury and/or failure, which may be caused by internal or external trauma (e.g. injury), or by an infection.

Such conditions may thus result from sepsis or septic shock caused by a viral, bacterial or fungal infection (e.g. a viral respiratory tract infection). Furthermore, acute lung injury, ARDS and, particularly, SARS may be caused by viruses, such as coronaviruses, include the novel SARS coronavirus 2 (SARS-CoV-2), which may result in internal tissue damage and/or dysfunction of relevant internal (e.g. mucosal) tissues, such as the respiratory epithelium, and so result in virally-induced pneumonia, impaired lung function, respiratory dysfunction, distress and/or failure. Such tissue damage may also give rise to severe fibrosis. For example, the SARS disease caused by the novel coronavirus SARS-CoV-2 (coronavirus disease 2019 or COVID-19) is known in many cases to result in fibrosis.

Compounds of the invention are particularly useful in the treatment of a disease or condition in which activation of AT2 receptors is desired or required but in which inhibition of one or more CYP enzymes is not desired.

In an alternative embodiment of the invention, there is provided the use of a compound of formula I, or a pharmaceutically acceptable salt thereof, in the manufacture of a medicament for use in the treatment of a disease or condition in which activation of AT2 receptors is desired or required but in which inhibition of CYP enzymes is not desired.

By a 'disease or condition in which activation of AT2 receptors is desired or required but in which inhibition of CYPs is not desired', we include diseases or conditions that are known to be treatable by activation of AT2 receptors, such as those mentioned hereinafter, but wherein existing treatments of such conditions may comprise administration of other therapeutic agents that are metabolized by CYPs. Such diseases or conditions may thus include conditions in which inhibition of at least one CYP enzyme is not required, advantageous and/or desirable, or in which such inhibition is or would be detrimental to the patient.

Particular diseases or condition in which activation of AT2 receptors is desired or required but in which inhibition of CYP enzymes is not desired are interstitial lung diseases (e.g. pulmonary fibrosis, IPF, systemic sclerosis and sarcoidosis), autoimmune diseases (e.g. rheumatoid arthritis, systemic lupus erythematosus, multiple sclerosis, psoriasis and inflammatory bowel disease), chronic kidney diseases (e.g. diabetic nephropathy), pulmonary hypertension, pulmonary arterial hypertension, preeclampsia and/or infarction (e.g. myocardial infarction and stroke). Thus, compounds of the invention are particularly useful in the treatment of interstitial lung diseases, such as IPF; autoimmune diseases, such as rheumatoid arthritis; chronic kidney diseases, such as diabetic nephropathy; pulmonary hypertension, including pulmonary arterial hypertension; preeclampsia; and/or infarction, such as myocardial infarction.

According to a further aspect of the present invention, there is provided a method of treatment of a disease or condition in which activation of AT2 receptors is desired or required but in which inhibition of CYP enzymes is not desired (such as pulmonary fibrosis, in particular IPF), which method comprises administration of a therapeutically effective amount of a compound of the invention to a person suffering from the relevant condition.

The compounds of the invention are indicated both in the therapeutic, palliative, and/or diagnostic treatment, as well as the prophylactic treatment (by which we include preventing and/or abrogating deterioration and/or worsening of a condition) of any of the above conditions.

Compounds of the invention will normally be administered orally, intravenously, subcutaneously, buccally, rectally, dermally, nasally, tracheally, bronchially, by any other parenteral route, or via inhalation or pulmonary route, or any combination thereof, in a pharmaceutically acceptable dosage form, in solution, in suspension, in emulsion, including nanosuspensions, or in liposome formulation. Additional methods of administration include, but are not limited to, intraarterial, intramuscular, intraperitoneal, intraportal, intradermal, epidural, intrathecal administration, or any combination thereof.

In some embodiments, the compounds of the invention may be administered alone (e.g. separately), and/or sequentially, and/or in parallel at the same time (e.g. concurrently), using different administrative routes, but are preferably administered by way of known pharmaceutical formulations, including tablets, capsules or elixirs for oral administration, suppositories for rectal administration, sterile solutions, suspensions or emulsions for parenteral or intramuscular administration, or via inhalation, and the like. Administration through inhalation is preferably done by using a nebulizer, thus delivering the compound of the invention to the small lung tissue including the alveoli and bronchioles, preferably without causing irritation or cough in the treated subject.

Preferably, administration of a therapeutically effective amount of a compound of the invention is performed by a combination of administrative routes, either separately (e.g. about 2 or more hours apart from one another), sequentially (e.g. within about 2 hours of one another), or in parallel at the same time (e.g. concurrently), including via inhalation and orally, achieving an effective dosage.

In some embodiments, there is provided a method of treating a disease or condition in which activation of AT2 receptors is desired or required (and such diseases or conditions in which inhibition of CYP enzymes is not desired), including pulmonary fibrosis, and in particular IPF, which method comprises administering a therapeutically effective amount of a compound of the invention through a combination of administrative routes, either separately, sequentially, or in parallel at the same time, preferably via inhalation and orally, in order to achieve effective amount or dosage, to a patient in need of such a therapy.

Such combinations of administrative routes, preferably via inhalation and orally, may be presented as separate formulations of the compound of invention that are optimized for each administrative route.

Such formulations may be prepared in accordance with standard and/or accepted pharmaceutical practice.

According to a further aspect of the invention there is thus provided a pharmaceutical formulation comprising a compound of the invention, in admixture with a pharmaceutically acceptable adjuvant, diluent or carrier.

Compounds of the invention may be administered in combination with other AT2 agonists that are known in the art, such as C21, as well as in combination with AT1 receptor antagonists that are known in the art, and/or in combination with an inhibitor of angiotensin converting enzyme (ACE). Non-limiting but illustrative examples of AT1 receptor antagonists that can be used according to the embodiments include azilsartan, candesartan, eprosartan, fimasartan, irbesartan, losartan, milfasartan, olmesartan, pomisartan, pratosartan, ripiasartan, saprisartan, tasosartan, telmisartan, valsartan and/or combinations thereof. Non-limiting but illustrative examples of ACE inhibitors that can be used according to the embodiments include captopril, zofenopril, enalapril, ramipril, quinapril, perindopril, lisinopril, benazepril, imidapril, trandolapril, fosinopril, moexipril, cilazapril, spirapril, temocapril, alacepril, ceronapril, delepril, moveltipril, and/or combinations thereof.

Other active ingredients that may be administered in combination with compounds of the invention include disodium cromoglycate; endothelin receptor antagonists, such as bosentan, ambrisentan, sitaxentan and macitentan; PDE5 inhibitors, such as sildenafil and tadalafil: prostacyclin (epoprostenol) and analogues thereof, such as iloprost and treprostinil; other biologics including interferon gamma-1b, etanercept, infliximab and adalimumab; and methotrexate. Further active ingredients in development that may be co-administered with compounds of the invention include pamrevlumab (anti-CTGF, Fibrogen); GLPG1690 (autotaxin inhibitor, Galapagos), TD139 (Galectin-3 inhibitor, Galecto), PRM-151 (recombinant pentraxin-2, Promedior), BBT-877 (autotaxin inhibitor, Boehringer/Bridge), CC-90001 (JNK inhibitor, Celgene), PBI-4050 (dual GPR40 agonist/GPR84 antagonist, Prometic), BMS-986020 (lysophosphatidic acid receptor antagonist, BMS), RVT-1601 (mast cell stabilizer, Respivant), SM04646 (wnt-signal inhibitor, United Therapeutics), KD25 (Rho associated kinase inhibitor, Kadmon Holdings), BG00011 (integrin antagonist, Biogen), PLN-74809 (integrin antagonist, Pilant Therapeutics), Saracatinib (src kinase inhibitor, AstraZeneca), PAT-1251 (lysyloxidase inhibitor 2, PharmAkea), ABM-125 (IL-25 MAB, Abeome) and TA5-115 (multi-kinase inhibitor, Otsuka).

In a further aspect of the invention, compounds of the invention find particular utility when combined with other therapeutic agents in combination therapy to treat the various conditions, including those mentioned hereinbefore. Because compounds of the invention exhibit minimal CYP enzyme inhibition, such combinations are particularly advantageous when the other therapeutic agents that are employed for use in the relevant condition are themselves metabolized by CYP enzymes.

Thus, when the condition to be treated is an interstitial lung disease, such as IPF, systemic sclerosis or fibrotic diseases that are known in the art, compounds of the invention are preferably administered in combination with a Galectin-3 inhibitor, a lysophosphatidic acid receptor 1 (LPA1) antagonist, an autotaxin (ATX) inhibitor, a recombinant human pentraxin-2 protein or established therapies for such treatment, including but not limited to pirfenidone and/or nintedanib. Preferably, the combination of compound of the invention is with pirfenidone, or a pharmaceutically-acceptable salt thereof, which compound is known to be metabolized by CYP enzymes, such as CYP1A.

Further, when the condition to be treated is a chronic kidney related disease, compounds of the invention are preferably administered in combination with one or more other drugs that are also used in such treatments, such as irbesartan and/or torsemide, which compounds are known to be metabolized by CYP enzymes, such as CYP2C9.

When the condition to be treated is pulmonary hypertension, compounds of the invention are preferably administered in combination with one or more other drugs that are also used in such treatment, such as selexipag and/or sildenafil, which compounds are known to be metabolized by CYP enzymes, such as CYP3A4.

When the condition to be treated or prevented is myocardial infarction and/or a stroke-related disease, compounds of the invention are preferably administered in combination with one or more other drugs that are also used in such treatment, such as propranolol, warfarin, clopidogrel, atorvastatin, cilostazol, lidocaine and/or simvastatin, or a pharmaceutically-acceptable salt thereof, which compounds are known to be metabolized by CYP enzymes, such as CYP1A, CYP2CP and/or CYP3A4.

When the condition to be treated is an autoimmune disease, such as rheumatoid arthritis, multiple sclerosis or psoriasis, compounds of the invention are preferably administered in combination with one or more other drugs that are also used in such treatment, including but not limited to non-steroidal anti-inflammatory drugs (NSAIDs), such as naproxen, celecoxib, meloxicam or an analogue thereof (e.g. piroxicam) orindomethacin; or a drug such as tizanidine, cyclophosphamide, cyclosporine, deflazacort and/or hydrocortisone, riluzole, or a pharmaceutically-acceptable salt thereof, which compounds are known to be metabolized by CYP enzymes, such as CYP1A, CYP2CP, CYP2C19 and/or CYP3A4.

Thus, compounds of the invention are particularly useful in the treatment of a disease or condition in which activation of the AT2 receptor is desired or required but in which inhibition of CYP enzymes is not desired and so may be administered to treat diseases, including those mentioned hereinbefore, in combination with one or more of the other therapeutic agents mentioned hereinbefore, which are metabolized through a CYP enzyme pathway, is or may be useful, including pirfenidone, naproxen, propranolol, riluzole, tizanidine, warfarin, celecoxib, clopidogrel, irbesartan, meloxicam, piroxicam, torsemide, cyclophosphamide, indomethacin, atorvastatin, cilostazol, cyclosporine, deflazacort, hydrocortisone, lidocaine, selexipag, sildenafil and/or simvastatin. Most preferably, the compounds of the invention are administered in combination with pirfenidone to treat an interstitial lung disease, such as IPF, Therapeutic agents that may be used in conjunction with compounds of the invention include variously-applied standard treatments for viral infections, including antibody therapies (e.g. LY-CoV555/LY-CoV016 (bamlanivimab and etesevimab), LY-CoV555 (bamlanivimab, Eli Lilly), REGN-COV2 (casirivimab and imdevimab), REGN3048-3051, TZLS-501, SNG001 (Synairgen), eculizumab (Soliris; Alexion Pharmaceuticals), ravulizumab (Ultomiris; Alexion Pharmaceuticals), lenzilumab, leronlimab, tocilizumab (Actemra; Roche), sarilumab (Kevzara; Regeneron Pharma), and Octagam (Octapharma)), antiviral medicines (e.g. oseltamivir, remdesivir, favilavir, molnupiravir, simeprevir, daclatasvir, sofosbuvir, ribavirin, umifenovir, lopinavir, ritonavir, lopinavir/ritonavir (Kaletra; AbbVie Deutschland GmbH Co. KG), teicoplanin, baricitinib (Olumiant; Eli Lilly), ruxolitinib (Jakavi; Novartis), tofacitinib (Xeljanz; Pfizer), the TMPRSS2 inhibitor camostat, or camostat mesylate, Actemra (Roche), AT-100 (rhSP-D), MK-7110 (CD24Fc; Merck)), OYA1 (OyaGen9), BPI-002 (BeyondSpring), NP-120 (Ifenprodil; Algernon Pharmaceuticals), and Galidesivir (Biocryst Pharma), anti-inflammatory agents (e.g. NSAIDs, such as ibuprofen, ketorolac, naproxen, and the like), chloroquine, hydroxychloroquine, interferons (e.g. interferon beta (interferon beta-1a), tocilizumab (Actemra), lenalidomide, pomalidomide and thalidomide), analgesics (e.g. paracetamol or opioids), antitussive agents (e.g. dextromethorphan), vaccinations (e.g. INO-4800 by Inovio Pharmaceuticals and Beijing Advaccine Biotechnology, if available), COVID-19 convalescent plasma (CCP) and/or passive antibody therapy with antibodies from blood of people who have recovered from infection with SARS-CoV or SARS-CoV-2.

Further therapeutic agents that may be mentioned include anti-fibrotics (e.g. nintedanib and, particularly, pirfenidone), vitamins (e.g. vitamin B, C and D) and mucolytics such as acetylcysteine and ambroxol.

Other therapeutic agents that may be used in conjunction with compounds of the invention or pharmaceutically acceptable salts thereof in accordance with the invention include corticosteroids. Corticosteroids include both naturally-occurring corticosteroids and synthetic corticosteroids.

Naturally-occurring corticosteroids that may be mentioned include cortisol (hydrocortisone), aldosterone, corticosterone, cortisone, pregnenolone, progesterone, as well as naturally-occurring precursors and intermediates in corticosteroid biosynthesis, and other derivatives of naturally-occurring corticosteroids, such as 11-deoxycortisol, 21-deoxycortisol, 11-dehydrocorticosterone, 11-deoxycorticosterone, 18-hydroxy-11-deoxycorticosterone, 18-hydroxycorticosterone, 21-deoxycortisone, 11β-hydroxypregnenolone, 11β,17α,21-trihydroxypregnenolone, 17α,21-dihydroxypregnenolone, 17α-hydroxypregnenolone, 21-hydroxypregnenolone, 11-ketoprogesterone, 11β-hydroxyprogesterone, 17α-hydroxyprogesterone and 18-hydroxyprogesterone.

Synthetic corticosteroids that may be mentioned include those of the hydrocortisone-type (Group A), such as cortisone acetate, hydrocortisone aceponate, hydrocortisone acetate, hydrocortisone buteprate, hydrocortisone butyrate, hydrocortisone valerate, tixocortol and tixocortol pivalate, prednisolone, methylprednisolone, prednisone, chloroprednisone, cloprednol, difluprednate, fludrocortisone, fluocinolone, fluperolone, fluprednisolone, loteprednol, prednicarbate and triamcinolone; acetonides and related substances (Group B), such as amcinonide, budesonide, desonide, fluocinolone cetonide, fluocinonide, halcinonide, triamcinolone acetonide, ciclesonide, deflazacort, formocortal, fludroxycortide, flunisolide and fluocinolone acetonide, those of the (beta)methasone-type (Group C), such as beclomethasone, betamethasone, betamethasone dipropionate and betamethasone valerate, dexamethasone, fluocortolone, halometasone, mometasone and mometasone furoate, alclometasone and alclometasone dipropionate, clobetasol and clobetasol propionate, clobetasone and clobetasone butyrate, clocortolone, desoximetasone, diflorasone, difluocortolone, fluclorolone, flumetasone, fluocortin, fluprednidene and fluprednidene acetate, fluticasone, fluticasone furoate and fluticasone propionate, meprednisone, paramethasone, prednylidene, rimexolone and ulobetasol; those of the progesterone-type, such as flugestone, fluorometholone, medrysone and prebediolone acetate, and progesterone derivatives (progestins), such as chlormadinone acetate, cyproterone acetate, medrogestone, medroxyprogesterone acetate, megestrol acetate and segesterone acetate; as well as other corticosteroids, such as cortivazol and 6-methyl-11β,17β-dihydroxy-17α-(1-propynyl)androsta-1,4,6-trien-3-one.

Preferred corticosteroids include cortisone, prednisone, prednisolone, methylprednisolone and, especially, dexamethasone.

Further, therapeutic agents that may be used in conjunction with compounds of the invention or pharmaceutically acceptable salts thereof include H2 receptor blockers, anticoagulants, anti-platelet drugs, as well as statins, antimicrobial agents and anti-allergic/anti-asthmatic drugs.

H2 receptor blockers that may be mentioned include famotidine. Anticoagulants that may be mentioned include heparin and low-molecular-weight heparins (e.g. bemiparin, nadroparin, reviparin, enoxaparin, parnaparin, certoparin, dalteparin, tinzaparin); directly acting oral anticoagulants (e.g. dabigatran, argatroban, rivaroxaban, apixaban, edoxaban, betrixaban, darexaban, otamixaban, letaxaban, eribaxaban, hirudin, lepirudin and bivalirudin); coumarin type vitamin K antagonists (e.g. coumarin, acenocoumarol, phenprocoumon, atromentin and phenindione) and synthetic pentasaccharide inhibitors of factor Xa (e.g. fondaparinux, idraparinux and idrabiotaparinux). Anti-platelet drugs that may be mentioned include irreversible cyclooxygenase inhibitors (e.g. aspirin and triflusal); adenosine diphosphate receptor inhibitors (e.g. cangrelor, clopidogrel, prasugrel, ticagrelor and ticlopidine); phosphodiesterase inhibitors (e.g. cilostazol); protease-activated receptor-1 antagonists (e.g. vorapaxar); glycoprotein IIB/IIIA inhibitors (e.g. abciximab, eptifibatide and tirofiban); adenosine reuptake inhibitors (e.g. dipyridamole); and thromboxane inhibitors (e.g. terutroban, ramatroban, seratrodast and picotamide).

Statins that may be mentioned include atorvastatin, simvastatin and rosuvastatin. Antimicrobial agents that may be mentioned include azithromycin, ceftriaxone, cefuroxime, doxycycline, fluconazole, piperacillin, tazobactam and teicoplanin. Anti-allergic/anti-asthmatic drugs that may be mentioned include chlorphenamine, levocetirizine and montelukast.

Subjects may thus also (and/or may be already) be receiving one or more of any of the other therapeutic agents mentioned above, by which we mean receiving a prescribed dose of one or more of those other therapeutic agents, prior to, in addition to, and/or following, treatment with compounds of the invention or pharmaceutically acceptable salts thereof.

When compounds of the invention are "combined" with other therapeutic agents as mentioned hereinbefore, the active ingredients may be administered together in the same formulation, or administered separately (simultaneously or sequentially) in different formulations.

Such combination products provide for the administration of compounds of the invention in conjunction with the other therapeutic agent, and may thus be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the other therapeutic agent).

Thus, there is further provided:

(1) a pharmaceutical formulation including a compound of the invention; a therapeutic agent selected from those described above (e.g. one that is known to be metabolized by a CYP enzyme); and a pharmaceutically-acceptable excipient (e.g. adjuvant, diluent or carrier), which formulation is hereinafter referred to as a "combined preparation"; and (2) a kit of parts comprising components:

(A) a pharmaceutical formulation including a compound of the invention in admixture with a pharmaceutically-acceptable adjuvant, diluent or carrier; and (B) a pharmaceutical formulation including a therapeutic agent selected from those described above (e.g. one that is known to be metabolized by a CYP enzyme), in admixture with a pharmaceutically-acceptable adjuvant, diluent or carrier, which components (A) and (B) are each provided in a form that is suitable for administration in conjunction with the other.

In a further aspect of the invention, there is provided a process for the preparation of a combined preparation as hereinbefore defined, which process comprises bringing into association a compound of the invention, the other therapeutic agent, and at least one (e.g. pharmaceutically-acceptable) excipient.

In a further aspect of the invention, there is provided a process for the preparation of a kit-of-parts as hereinbefore defined, which process comprises bringing into association components (A) and (B). As used herein, references to bringing into association will mean that the two components are rendered suitable for administration in conjunction with each other.

Thus, in relation to the process for the preparation of a kit-of-parts as hereinbefore defined, by bringing the two components "into association with" each other, we include that the two components of the kit-of-parts may be:

(i) provided as separate formulations (i.e. independently of one another), which are subsequently brought together for use in conjunction with each other in combination therapy; or (ii) packaged and presented together as separate components of a "combination pack" for use in conjunction with each other in combination therapy.

Thus, there is further provided a kit-of-parts comprising:

(I) one of components (A) and (B) as defined herein; together with (II) instructions to use that component in conjunction with the other of the two components.

Depending upon the patient to be treated and the route of administration, the compounds of the invention may be administered at varying doses. Although doses will vary from patient to patient, suitable daily doses are in the range of about 0.1 to about 1000 mg (e.g. 0.1, 0.5, 1, 2, 5, 10, 15, 20, 25, 30, 35, 40, 45, 50, 75, 100, 150, 200, 250, 300, 350, 400, 450, 500, 550, 600, 650, 700, 750, 800, 850, 900, 950, 1000 mg, and the like, or any range or value therein) per patient, administered in single or multiple doses. More preferred daily doses are in the range of about 0.1 to about 250 mg (e.g., 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250 mg, and the like, or any range or value therein) per patient. A particular preferred daily dose is in the range of from about 0.3 to about 100 mg per patient.

Individual doses of compounds of the invention may be in the range of about 0.1 to about 100 mg (e.g. 0.3, 0.5, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100 mg, and the like, or any range or values therein).

In any event, the physician, or the skilled person, will be able to determine the actual dosage, which will be most suitable for an individual patient, which is likely to vary with the condition that is to be treated, as well as the age, weight, sex and response of the particular patient to be treated. The above-mentioned dosages are exemplary of the average case, there can, of course, be individual instances where higher or lower dosage ranges are merited, and such are within the scope of this invention.

The benefits of using the compounds of the invention via a combination of administrative routes, separately, and/or sequentially, and/or in parallel at the same time is to produce a tailored treatment for the patient in need of the therapy, with the possibility of preventing and/or reducing side effects, and also tune the correct dosage levels of a therapeutically effective amount of a compound of the invention.

The kits of parts described herein may comprise more than one formulation including an appropriate quantity/dose of a compound of the invention, and/or more than one formulation including an appropriate quantity/dose of the other therapeutic agent, in order to provide for repeat dosing. If more than one formulation (comprising either active compound) is present, such formulations may be the same, or may be different in terms of the dose of either compound, chemical composition(s) and/or physical form(s).

With respect to the kits of parts as described herein, by "administration in conjunction with", we include that respective formulations comprising a compound of the invention and other therapeutic agent are administered, sequentially, separately and/or simultaneously, over the course of treatment of the relevant condition.

Thus, in respect of the combination product according to the invention, the term "administration in conjunction with" includes that the two components of the combination product (compound of the invention and other therapeutic agent) are administered (optionally repeatedly), either together, or sufficiently closely in time, to enable a beneficial effect for the patient, that is greater, over the course of the treatment of the relevant condition, than if either a formulation comprising compound of the invention, or a formulation comprising the other agent, are administered (optionally repeatedly) alone, in the absence of the other component, over the same course of treatment. Determination of whether a combination provides a greater beneficial effect in respect of, and over the course of treatment of, a particular condition will depend upon the condition to be treated or prevented, but may be achieved routinely by the skilled person.

Further, in the context of a kit-of-parts according to the invention, the term "in conjunction with" includes that one or other of the two formulations may be administered (optionally repeatedly) prior to, after, and/or at the same time as, administration of the other component. When used in this context, the terms "administered simultaneously" and "administered at the same time as" include that individual doses of the relevant compound of the invention and other antiinflammatory agent are administered within 48 hours (e.g. 24 hours) of each other.

Pharmaceutical compositions/formulations, combination products and kits as described herein may be prepared in accordance with standard and/or accepted pharmaceutical practice.

Thus, in a further aspect of the invention there is provided a process for the preparation of a pharmaceutical composition/formulation, as hereinbefore defined, which process comprises bringing into association certain compounds of the invention, as hereinbefore defined, with one or more pharmaceutically-acceptable excipients (e.g. adjuvant, diluent and/or carrier).

In further aspects of the invention, there is provided a process for the preparation of a combination product or kit-of-parts as hereinbefore defined, which process comprises bringing into association certain compounds of the invention, as hereinbefore defined, with the other therapeutic agent that is useful in the treatment of the relevant disease or disorder, and at least one pharmaceutically-acceptable excipient.

Subjects suitable to be treated with formulations of the present invention include, but are not limited to, mammalian subjects, in particular human subjects.

When used herein in relation to a specific value (such as an amount), the term "about" (or similar terms, such as "approximately") will be understood as indicating that such values may vary by up to 10% (particularly, up to 5%, such as up to 1%) of the value defined. It is contemplated that, at each instance, such terms may be replaced with the notation "10%", or the like (or by indicating a variance of a specific amount calculated based on the relevant value). It is also contemplated that, at each instance, such terms may be deleted.

Compounds of the invention have the advantage that they are more potent than, and/or are stable to metabolic hydrolysis, and/or do not inhibit the CYP enzymes mentioned hereinbefore.

The compounds of the invention may also have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties than compounds known in the prior art, whether for use in the treatment of IPF or otherwise.

Such effects may be evaluated clinically, objectively and/or subjectively by a health care professional, a treatment subject or an observer.

EXAMPLES

The invention will be further described by reference to the following examples, which are not intended to limit the scope of the invention.

In the event that there is a discrepancy between nomenclature and any compounds depicted graphically, then it is the latter that presides (unless contradicted by any experimental details that may be given or unless it is clear from the context).

Experimental Procedures

Starting materials and intermediates used in the synthesis of compounds described herein are commercially available or can be prepared by the methods described herein or by methods known in the art.

Experiments were generally carried out under inert atmosphere (nitrogen or argon), particularly in cases where oxygen- or moisture-sensitive reagents or intermediates were used.

Mass spectrometry data are reported from liquid chromatography-mass spectrometry (LC-MS). Chemical shifts for NMR data are expressed in parts per million (ppm, 5) referenced to residual peaks from the deuterated solvent used.

For syntheses referencing general procedures, reaction conditions (such as length of reaction or temperature) may vary. In general, reactions were followed by thin layer chromatography or LC-MS, and subjected to work-up when appropriate. Purifications may vary between experiments: in general, solvents and the solvent ratios used for eluents/gradients were chosen to provide an appropriate R and/or retention time. Some products were purified using supercritical fluid chromatography, for example on a reversed phase column using solvent combinations with mobile phase A; $CO_2$ and B: MeOH/$H_2O$/NH3. Some compounds were purified using preparative HPLC, flash column chromatography or manual C18 reverse column with $H_2O$/MeCN polarity.

EXAMPLES

Example 1

Furan-2-ylmethyl-3-[[5-isobutyl-3-[4-[(2-tert-butylimidazol-1-yl)methyl]phenyl]-2-thienyl]sulfonyl]urea

(a) 1-[(4-Bromophenyl methyl]-2-tert-butyl-imidazole

NaH (0.184 g, 8.0 mmol, 2 equiv.) was added to a stirred solution of 2-tert-butyl-1H-imidazole (0.497 g, 4.0 mmol, 1 equiv.) in DMF (0.27 M) at 0° C. After 20 min 1-bromo-4-(bromomethyl)benzene (1.05 g, 4.2 mmol, 1.05 equiv.) was added. The resulting mixture was allowed to warm to ambient temperature and stirred overnight, then quenched with water (15 mL). The product was extracted with ethyl acetate (3×25 mL). The combined organic layers were washed with brine (20 mL), dried over anhydrous $MgSO_4$ and concentrated in vacuo. The title compound was afforded as a solid in 99% yield (1.16 g, 0.396 mmol).

(b) 5-Bromo-N-(tert-butyl)thiophene-2-sulfonamide

5-Bromothiophene-2-sulfonyl chloride (1 mmol, 1 equiv.) was dissolved in DCM (2 mL) and tert-butylamine (1.1 mmol, 1.1 equiv.) was added and the reaction mixture was stirred for 2-4 hours. The sub-title product was isolated by flash column (20% EtOAc in isohexane) as a colourless solid.

(c) N-tert-Butyl-5-isobutylthiophene-2-sulfonamide

The sub-title product was prepared following method A and B below.

Method A: Zinc chloride (1.9 M in 2-metyltetrahydrofuran) was added to a dry vial and capped. Iso-butylmagnesium chloride (2.0 M in THF) was added slowly and the mixture was stirred for 15 minutes. 5-Bromo-N-(tert-butyl)thiophene-2-sulfonamide (from step (b) above) and $Pd(tBu_3P)_2$ were dissolved in dry THF (0.75 mL) and added to the vial. The reaction mixture was heated under microwave irradiation at 80° C. for 30 minutes.

Method B: Under nitrogen, $Pd(OAc)_2$ was combined with Xantphos in degassed THF. After stirring for 5 minutes, the solution was transferred to a separate vessel under nitrogen containing 5-bromo-N-(tert-butyl)thiophene-2-sulfonamide and iso-butylzinc bromide. The sealed vessel was heated at 80° C. for 18 hours.

In both of Methods A and B, upon cooling to room temperature, the reaction mixture was filtered and the solid was washed with DCM. The solvents were removed by rotary evaporation and the sub-title compound was purified by column chromatography (20% EtOAc in isohexane) as colourless solid.

(d) N-(tert-butyl)-5-isobutyl-3-(6-methyl-4,8-dioxo-1,3,62-dioxazaborocan-2-yl)thiophene-2-sulfonamide N-tert-Butyl-5-isobutylthiophene-2-sulfonamide (1.00 g, 3.65 mmol; from step (c) above) was dissolved in dry THF and transferred to a dry 3-necked round bottom flask. The flask was evacuated three times and placed under inert atmosphere. The mixture was cooled to −78° C. and n-BuLi (7.59 mL, 19.0 mmol, 4.74 equiv.) was added dropwise. The mixture was stirred for 30 min at −78° C. before it was transferred to an ice bath and stirred at 0° C. for 45 min to afford an orange solution. The mixture was again place in a dry ice bath and tri-isopropyl borate (2.53 mL, 10.9 mmol) was added over 5 minutes using a syringe. The solution was stirred for 15 minutes before it was transferred back to an ice bath and stirred for 1 h during which formation of white precipitate was observed.

To the now white, and non-transparent, solution was added 2 M HCl (aq.; 20 mL) and the solution was stirred for 15 minutes. Partial evaporation of the mixture was performed to remove the majority of the THF present. The remaining mixture was diluted with water (10 mL) and extracted with DCM (3×25 mL). The combined organic layers were dried with $MgSO_4$ and the solvent was removed under reduced pressure.

The crude boronic acid was dissolved in DMSO (2 mL) and toluene (30 mL). Methyliminodiacetic acid (0.748 g, 5.09 mmol) was added and the mixture was refluxed for 3 h. The reaction mixture was allowed to cool to room temperature over 1 h.

The mixture was diluted with EtOAc (100 mL) and subsequently washed with 0.1 M aq. HCl (3×50 mL). The organic phase was dried with $MgSO_4$ and the solvent was removed under reduced pressure. The crude product was purified by FCC (10-100% ethyl acetate in isohexane) to afford the product as pale yellow amorphous solid (1.56 g, 77% yield). $^1H$ NMR (400 MHz, Chloroform-d) δ 6.87 (d, J=0.8 Hz, 1H), 5.20 (s, 1H), 3.98 (m, 4H), 2.82 (s, 3H), 2.66 (d, J=7.6 Hz, 2H), 1.89 (m, 1H), 1.25 (s, 9H), 0.93 (d, J=6.6 Hz, 6H).

(e) 3-(4-((2-(tert-Butyl)-1H-imidazol-1-yl)methyl)phenyl)-5-isobutylthiophene-2-sulfonamide N-(tert-butyl)-5-isobutyl-3-(6-methyl-4,8-dioxo-1,3,6,2-dioxazaborocan-2-yl)thiophene-2-sulfonamide (from step (d) above; 0.451 g, 1.05 mmol), $K_2CO_3$ (0.415 g, 3.00 mmol, 3 equiv.), 1-[(4-bromophenyl)methyl]-2-tert-butyl-imidazole (see step (a) above; 0.293 g, 1.0 mmol) and $Pd(PPh_3)_4$ (57.8 g, 0.50 mmol, 0.05 equiv.) were suspended in degassed toluene (6 mL), ethanol (2 mL) and water (1 mL). The resulting reaction mixture was stirred at 120° C. for 60 min under microwave irradiation, then allowed to cool to ambient temperature, water (10 mL) was added and the reaction mixture extracted with ethyl acetate (2×25 mL). The combined organic layers were washed with brine (25 mL), dried over anhydrous $Na_2SO_4$ and concentrated. The crude product was purified by FCC (0-10% MeOH in $CH_2C_2$) to afford the sub-title compound as a pale yellow amorphous solid (0.364 g, 75% yield over two steps, 90% purity). $^1$H-NMR (400 MHz, Chloroform-d) δ 7.53 (d, J=7.8 Hz, 2H), 7.31 (s, 1H), 7.19-6.93 (m, 3H), 6.69 (s, 1H), 5.76 (s, br., 2H), 5.46 (s, 2H), 2.61 (d, J=7.0 Hz, 2H), 2.12-1.78 (m, 1H), 1.49 (s, 9H), 0.92 (d, J=6.6, 6H).

(f) Furan-2-ylmethyl-3-[[5-isobutyl-3-[4-[(2-tert-butyl-imidazol-1-yl)methyl]-phenyl]-2-thienyl]sulfonyl]urea 3-(4-((2-(tert-Butyl)-1H-imidazol-1-yl)methyl)phenyl)-5-isobutylthiophene-2-sulfon-amide (from step (f) above; 0.12 mmol, 1 equiv.) and copper (I) chloride (0.02 mmol, 15 mol %) were dissolved in dry DMF at room temperature, and under an argon atmosphere 2-(isocyanatomethyl)furan (0.35 mmol, 2.5 equiv.) was added and the reaction mixture was stirred for 24 h. After the completion of the reaction, the crude mixture was poured into 0.1 N aqueous HCl, diluted with ethyl acetate (25 mL), and the organic and aqueous phases were separated. The aqueous phase was extracted twice with ethyl acetate (20 mL), the combined organic phases were washed with brine (20 mL), dried over $MgSO_4$, and the solvent was evaporated in vacuo to give the crude product. The crude product was purified with preparative HPLC (20-90% acetonitrile in water) and the product was obtained as white amorphous solid (36 mg, 56% yield). $^1$H-NMR (400 MHz, Acetonitrile-$d_3$) δ 7.51 (d, J=8.2 Hz, 2H), 7.40 (d, J=1.0 Hz, 1H), 7.12 (d, 1=8.2 Hz, 2H), 6.90 (brs, 2H), 6.85 (brs, 1H), 6.35 (dd, J=3.2, 1.9 Hz, 1H), 6.22-6.11 (m, 2H), 5.42 (s, 2H), 4.20 (d, J=5.7 Hz, 2H), 2.75 (d, J=7.1 Hz, 2H), 1.97-1.95 (m, 1H), 1.42 (s, 9H), 1.01 (d, J=6.6 Hz, 6H). $^{13}$C-NMR (101 MHz, Acetonitrile-$d_3$) δ 154.4, 153.2, 142.5, 138.0, 137.9, 134.6, 130.1, 130.0, 126.9, 126.8, 124.6, 123.2, 111.1, 110.9, 108.1, 107.3, 51.2, 39.1, 37.0, 33.8, 30.9, 29.5, 22.0. HRMS (ESI): calcd. for $C_{28}H_{35}N_4O_4S_2^+$ $[M+H]^+$ 555.2094; found: 555.2107.

When measuring $^1$H NMR in acetonitrile-$d_3$ (above), it was observed that one of the proton peaks was trapped in the acetonitrile solvent residual peak (the peak at 1.97-1.95 (in, 1H)). Therefore, $^1$H NMR is also measured in MeOD. $^1$H-NMR (400 MHz, Methanol-$d_4$) δ 7.46 (brs, 2H), 7.38 (d, J=1.8 Hz, 1H), 7.19 (brs, 2H), 7.03 (brs, 2H), 6.77 (s, 1H), 6.32 (dd, J=3.2, 1.8 Hz, 1H), 6.15 (d, J=3.1 Hz, 1H), 5.57 (s, 2H), 4.16 (s, 2H), 2.73 (d, J=7.0 Hz, 2H), 1.94 (dt, J=13.4, 6.7 Hz, 1H), 1.49 (s, 9H), 1.01 (d, J=6.6 Hz, 6H).

Example 2

Thiophen-2-ylmethyl-3-[[5-isobutyl-3-[4-[(2-tert-butyl-imidazol-1-yl)methyl]phenyl]-2-thienyl]sulfonylurea The title compound was prepared using an analogous process to that described in Example 1 above, with the exception that 2-(isocyanatomethyl)thiophene (0.30 mmol, 2.5 equiv.) was employed in the final step. The crude product was purified with preparative HPLC (20-90% acetonitrile in water) and the product was obtained as white amorphous solid (31 mg, 47% yield). $^1$H-NMR (400 MHz, Acetonitrile-$d_3$) δ 7.52 (d, J=7.8 Hz, 2H), 7.23 (dd, J=5.1, 1.3 Hz, 1H), 7.07 (d, J=8.3 Hz, 2H), 6.99 (brs, 2H), 6.91 (dd, J=5.1, 3.4 Hz, 1H), 6.90-6.84 (m, 2H), 6.83 (s, 1H), 5.43 (s, 2H), 4.33 (d, J=5.7 Hz, 2H), 2.71 (d, J=7.1 Hz, 2H), 1.95-1.86 (m, 1H), 1.41 (s, 9H), 0.98 (d, J=6.6 Hz, 6H). $^{13}$C-NMR (101 MHz, Acetonitrile-$d_3$) δ 154.2, 154.0, 149.5, 144.0, 143.3, 137.3, 135.3, 134.7, 130.1, 129.9, 127.2, 127.0, 125.9, 125.3, 123.6, 123.5, 51.4, 39.1, 38.7, 33.9, 30.9, 29.3, 22.0. HRMS (ESI): calcd. for $C_{28}H_3N_4O_3S_3^+$ $[M+H]^+$ 571.1866; found: 571.1864.

Example 3

2-Methoxyethyl-3-[[5-isobutyl-3-[4-[(2-tert-butyl-imidazol-1-yl)methyl]thenyl]-2-thienyl]sulfonylurea The title compound was prepared using an analogous process to that described in Example 1 above, with the exception that 1-isocyanato-2-methoxyethane (0.29 mmol, 2.5 equiv.) was employed in the final step. The crude product was purified with preparative HPLC (20-90% acetonitrile in water) and the product was obtained as white amorphous solid (31 mg, 47% yield). $^1$H-NMR (400 MHz, Acetonitrile-$d_3$) δ 7.55 (d, J=8.2 Hz, 2H), 7.18 (d, 0.7=7.9 Hz, 2H), 6.99 (d, 0.7=1.6 Hz, 1H), 6.96 (d, 0.7=1.5 Hz, 1H), 6.87 (s, 1H), 6.14 (brs, 1H), 5.46 (s, 2H), 3.34 (t, J=5.5 Hz, 2H), 3.29 (s, 3H), 3.19 (q, J=5.5 Hz, 2H), 2.77 (d, J=7.0 Hz, 2H), 2.01-1.98 (m, 1H), 1.45 (s, 9H), 1.01 (d, 7=6.6 Hz, 6H). 13C-NMR (101 MHz, Acetonitrile-$d_3$) δ 154.3, 153.0, 150.1, 144.6, 144.2, 137.6, 134.6, 134.4, 130.1, 127.1, 123.8, 123.5, 71.4, 58.4, 51.4, 39.9, 39.1, 33.9, 30.9, 29.3, 22.0. HRMS (ESI): calcd. for $C_{26}H_{37}N_4O_4S_2^+$ $[M+H]^+$ 533.2251; found: 533.2252.

Example 4

Pyridin-2-ylmethyl-3-[[5-isobutyl-3-[4-[(2-tert-butyl-imidazol-1-yl)methyl]phenyl]-2-thienyl]sulfonylurea Sulfonamide (0.18 mmol, 1 equiv.), phenyl N-(2-pyridyl-methyl)carbamate (0.28 mmol, 1.5 equiv.; synthesized as described in Org. Biomol. Chem., 2017, 15, 4992) and DBU (0.28 mmol, 1.5 equiv.) were dissolved in acetonitrile and the reaction mixture was heated under MW for 1 h. After completion of the reaction, as indicated by TLC, the solvent was evaporated under reduced pressure. The residue was then dissolved in ethyl acetate and extracted with 0.1 N HCl. The aqueous phase was extracted twice with ethyl acetate (20 mL), the combined organic phases were washed with brine (20 mL), dried over $MgSO_4$, and the solvent was evaporated in vacuo to give the crude product. The crude product was purified with manual C-18 reverse column with water acetonitrile polarity (20-90% acetonitrile in water) and the product was obtained as white amorphous solid (60 mg, 57% yield). $^{1}$H-NMR (400 MHz, DMSO-$d_6$) δ 8.48 (d, J=4.2 Hz, 1H), 7.73 (td, J=7.7, 1.8 Hz, 1H), 7.55 (d, J=8.0 Hz, 2H), 7.26 (dd, J=7.0, 5.1 Hz, 1H), 7.14 (d, J=7.8 Hz, 1H), 7.09-7.07 (m, 3H), 6.92 (d, J=9.2 Hz, 2H), 6.84 (brs, 1H), 5.45 (s, 2H), 4.25 (d, J=5.5 Hz, 2H), 2.70 (d, J=7.1 Hz, 2H), 1.92-1.82 (m, 1H), 1.32 (s, 9H), 0.93 (d, J=6.6 Hz, 6H). $^{13}$C-NMR (101 MHz, DMSO-$d_6$) δ 163.5, 158.2, 153.7, 152.2, 149.3, 149.2, 144.0, 138.4, 137.2, 133.6, 130.0, 129.7, 126.4, 125.0, 123.3, 122.65, 121.3, 50.5, 44.9, 38.6, 33.6, 30.3, 30.0, 22.5. H RMS (ESI): calcd. For $C_{29}H_{36}N_5O_3S_2^+$ $[M+H]^+$ 566.2254; found: 566.2267.

Example 5

1-[[3-[4-[(2-Tert-butylimidazol-1-yl)methyl]-3-fluoro-phenyl]-5-isobutyl-2-thienyl]sulfonyl]-3-(2-pyridylmethyl)urea

(a) 1-(4-Bromo-2-fluorobenzyl)-2-(tert-butyl)-1H-imidazole

The sub-title compound was prepared using an analogous process to that described in Example 1, step (a) above, with the exception that 2-tert-butyl-1H-imidazole (1.02 g, 8.21 mmol) and 4-bromo-1-(bromomethyl)-2-fluoro-benzene (2.20 g, 8.21 mmol) were used instead. The crude product was purified by FCC (30% ethyl acetate in isohexane) to afford the product as a pale yellow amorphous solid (2.56 g, 39% yield). $^{1}$H-NMR (400 MHz, Chloroform-d) δ 7.24 (dd, J=9.5, 1.9 Hz, 1H), 7.21-7.16 (m, 1H), 6.93 (d, J=1.4 Hz, 1H), 6.67 (d, J=1.4 Hz, 1H), 6.55 (t, J=8.1 Hz, 1H), 5.25 (s, 2H), 1.35 (s, 9H). $^{13}$C-NMR (101 MHz, Chloroform-d) δ 159.4 (d, J=251.2 Hz), 154.6, 129.2 (d, J=4.5 Hz), 128.0 (d, J=3.7 Hz), 126.9, 124.0 (d, J=14.4 Hz), 122.0 (d, J=9.3 Hz), 121.6, 119.1 (d, J=24.1 Hz), 44.7 (d, J=4.9 Hz), 33.5, 29.8. $^{19}$F-NMR (376 MHz, Chloroform-d) 6-115.61 (t, J=8.7 Hz).

(b) 3-(4-((2-(Tert-butyl)-1H-imidazol-1-yl)methyl)-3-fluorophenyl)-5-isobutylthiophene-2-sulfonamide The sub-title compound was prepared using an analogous process to that described in Example 1, step C above. $^{1}$H-NMR (400 MHz, Chloroform-d) δ 7.48-7.31 (m, 3H), 7.15-6.97 (m, 2H), 6.72 (s, 1H), 5.78 (s, br., 2H), 5.48 (s, 2H), 2.64 (d, J=7.0 Hz, 2H), 1.98-1.81 (in, J=6.7 Hz, 1H), 1.56 (s, 9H), 0.96 (d, J=6.6 Hz, 6H). $^{13}$C-NMR (101 MHz, Chloroform-d) δ 159.9 (d, J=248.9 Hz), 152.8, 148.7, 141.1, 138.2 (d, J=8.4 Hz), 136.7, 129.2, 129.1, 126.2, 122.9, 120.7 (d, J=14.3 Hz), 119.7, 117.0 (d, J=21.9 Hz), 46.8 (d, J=3.4 Hz), 39.2, 33.9, 30.6, 28.7, 22.3. $^{19}$F-NMR (376 MHz, Chloroform-dl) 5-75.39.

(c) 1-[[3-[4-[(2-Tert-butylimidazol-1-yl)methyl]-3-fluoro-phenyl]-5-isobutyl-2-thienyl]sulfonyl]-3-(2-pyridylmethyl)urea 3-(4-((2-(Tert-butyl)-1H-imidazol-1-yl)methyl)-3-fluoro-phenyl)-5-isobutylthiophene-2-sulfonamide (450 mg, 330 μmol; from step (b) above), diphenyl carbonate (106 mg, 495 μmol) and $K_2CO_3$ (91 mg, 660 μmol) were dissolved in acetonitrile (15 ml) and the reaction was heated at 60° C. during the night under nitrogen atmosphere. The solids were filtered off and the solvent was evaporated. The crude material and 2-aminomethylpyridine (108 mg, 1 mmol) were dissolved in dioxane (10 ml). The reaction was heated to 70° C. during the night. The solvent was evaporated, and the product was purified using HPLC in an amount of 18 mg and isolated as $CF_3COOH$-salt. $^{1}$H-NMR ($CD_3OD$): 0.85 (d, 6H), 1.44 (s, 9H), 1.90 (m, 1H), 2.68 (d, 2H), 4.32 (s, 2H), 5.49 (s, 2H), 6.82 (s, 1H), 6.92 (m, 1H), 6.97 (s, 1H), 6.99 (s, 1H), 7.23-7.28 (b, 2H), 7.42 (d, 1H), 7.59 (d, 1H), 7.72 (d, 1H), 8.41 (d, 1H). MS [M+H]: 584.0, calculated 584.2.

Example 6

1-[[3-[4-[(2-Tert-butylimidazol-1-yl)methyl]-3-fluoro-phenyl]-5-isobutyl-2-thienyl]sulfonyl]-3-ethyl-urea 3-[4-[(2-tert-butylimidazol-1-yl)methyl]-3-fluoro-phenyl]-5-isobutyl-thiophene-2-sulfonamide (201 mg, 397 μmol; prepared as in Example 1, from step (b) above), ethyl isocyanate (94 μl, 1192 μmol) and $BF_3$-etherate (169 mg, 1192 μmol) were dissolved in acetonitrile (20 ml). After 4 hours at room temperature, LC/MS showed a small conversion to product. More ethyl isocyanate (94 μl, 1192 μmol) was added and the reaction was stirred during the night. The solvent was evaporated and the product was purified using HPLC in an amount of 84 mg and isolated as $CF_3COOH$-salt. $^{1}$H-NMR ($CDCl_3$): 0.98 (d, 6H), 1.04 (t, 3H), 1.63 (s, 9H), 1.93 (m, 1H), 2.70 (d, 2H), 3.14 (m, 2H), 5.51 (s, 2H), 6.76 (s, 1H), 7.11 (t, 1H), 7.23 (s, 1H), 7.27-7.35 (b, 3H). MS [M+H]: 521.0, calculated 521.2.

Example 7

1-[[3-[4-[(2-Tert-butylimidazol-1-yl)methyl]-3-fluoro-phenyl]-5-isobutyl-2-thienyl]sulfonyl]-3-(2-thienylmethyl)urea The title compound was prepared by a process that is analogous to that described in Example 5 above with the exception that 2-aminomethylthiophene (113 mg, 1000 μmol) was used. The product was isolated as $CF_3COOH$-salt in a yield of 70 mg. $^{1}$H-NMR ($CDCl_3$): 0.99 (d, 6H), 1.61 (s, 9H), 1.93 (m, 1H), 2.69 (d, 2H), 4.42 (d, 2H), 5.47 (s, 2H), 6.72 (s, 1H), 6.87 (m, 2H), 7.04 (b, 2H), 7.15 (d, 1H), 7.21 (m 2H), 7.32 (d, 1H). MS [M+H]: 589.0, calculated 589.2.

Biological Assays

The biological activity of example compounds as described herein above was assessed (and compared to $C_{21}$) using the following biological assays.

Metabolic Stability

Pooled human liver microsomes in PBS at a concentration of 0.5 mg/mL was incubated with or without 1 mM NADPH for 70 min at 37° C. Test compound was added after 10 minutes to a final concentration of 1 μM. Samples were withdrawn at 0, 5, 15 and 60 minutes and added to test tubes containing acetonitrile, to stop the reaction, and with terfenadine, used as internal standard. After centrifugation at 10 000×g for 5 minutes the supernatant was diluted 1:1 with 1% formic acid. Samples were separated on a reverse phase column and detected by triple quadrupole MSMS (Agilant model 6540). The concentration of the parent compound at the different time points was measured with an external standard curve using terfenadine as internal standard and the initial metabolic rate in the presence or absence of NADPH calculated.

| | $T_{1/2}$, no NaDPH [min] | $T_{1/2}$, + NaDPH [min] |
|---|---|---|
| C21 | 31 | 35 |
| Example 1 | >60 | >60 |
| Example 2 | >60 | 32 |
| Example 3 | >60 | >60 |
| Example 4 | >60 | >60 |
| Example 5 | >60 | >60 |
| Example 6 | >60 | >60 |
| Example 7 | >60 | 23 |

Binding to AT1 and AT2 Receptor

Compounds were evaluated for binding to the human recombinant AT2 and AT1 receptor according to Eurofins protocol ITEM26 and ITEM24 using a radiometric scintillation assay.

Briefly, for $IC_{50}$ measurements recombinant protein was incubated for 2-4 h at 37° C. with test compounds at concentration 1, 10, 100 and 1000 nM for the AT2 receptor and 1 and 10 μM for the AT1 receptor. Ki values for the AT2 receptor were determined using a seven-point dose-response curve. $^{125}$I(sar1,IIe8)-AT-II was used as a ligand for the AT1 receptor and $^{125}$ICGP 42112A was used as a ligand for the AT2 receptor. Percent inhibition of control specific binding was calculated according to 100−(measured specific binding/control specific binding)×100.

| | AT2R Ki [nM] | AT2 GraFit $IC_{50}$ [nM] | AT1 $IC_{50}$ [nM] |
|---|---|---|---|
| C21 | | 2.5 | 14,000 |
| C21 | | 3.2 | 10,000 |
| C21 | | 5.1 | 18,000 |
| C21 | | 3.6 | 13,000 |
| C21* | | 3.6 | 13,750 |
| Example 1 | | 2.6 | 3,000 |
| Example 1 | 2.8 | 5.7 | |
| Example 1* | | 4.2 | |
| Example 2 | | 2.5 | 2,000 |
| Example 2 | 1.25 | 2.5 | |
| Example 2* | | 2.5 | |
| Example 3 | 1.16 | 2.3 | 6,000 |
| Example 3 | | 9.7 | |
| Example 3* | | 6 | |
| Example 4 | 1.9 | 3.7 | |
| Example 4 | | 2.1 | 3,000 |
| Example 4* | | 2.9 | |
| Example 5 | | 0.44 | 1,800 |
| Example 6 | | 0.42 | 800 |
| Example 7 | | 5.0 | 3,100 |

An asterisk (*) represents the mean average of the data obtained from two runs.

CYP Inhibition

Compounds were evaluated at 10 μM for inhibition of the main cytochrome P450 isoforms (CYP1A, CYP2136, CYP2C8, CYP2C9, CYP2C19, CYP2D6, CYP3A4 and CYP3A4&5) using isoform-specific substrates incubated with human liver microsomes (Eurofins protocol ITEMG232). The following substrates were used; CYP1A phenacetin, CYP2136 bupropion, CYP2C8 paclitaxel and amodiaquine, CYP2C9 diclofenac, CYP2C19 omeprazole, CYP2D6 dextromethorphan, CYP3A midazolam and testosterone.

At the end of the incubation, the formation of metabolite was monitored by HPLC-MS/MS as the peak area response.

| | CYP1A Inh % | CYP2B6 Inh % | CYP2C19 Inh % | CYP2C8 Inh % | CYP2C9 Inh % | CYP2D6 Inh % |
|---|---|---|---|---|---|---|
| C21 | 91 | 49 | 96 | 80 | 99 | 81 |
| Example 1 | −13.2 | 96.5 | 49.1 | 77.8 | 58.4 | 13.8 |
| Example 2 | −1.8 | 9.6 | 56.8 | 81.8 | 64.6 | 33.6 |
| Example 4 | −0.5 | 13.8 | 44.4 | 79.3 | 43.5 | 24.3 |
| Example 5 | 34.1 | 24.9 | 52.1 | 78.3 | 62.1 | 23.2 |
| Example 6 | 15.8 | 27.0 | 35.1 | 77.6 | 39.7 | 18.8 |
| Example 7 | 20.7 | 50.5 | 49.1 | 79.9 | 76.3 | 13.8 |

| | CYP3A4 midazolam Inh % | CYP3A4&5 testosterone Inh % |
|---|---|---|
| C21 | 95 | 94 |
| Example 1 | 11.6 | 11.8 |
| Example 2 | 40.9 | 18.0 |
| Example 4 | 33.7 | 16.7 |
| Example 5 | 43.0 | 18.9 |
| Example 6 | 23.8 | 10.8 |
| Example 7 | 52.3 | 16.7 |

Abbreviations

The following abbreviations may be used herein.

DBU 1,8-Diazabicyclo(5.4.0)undec-7-ene

DCM dichloromethane

DMF dimethylformamide

DMSO dimethylsulfoxide

EtOAc ethyl acetate

FCC flash column chromatography

HPLC high-performance liquid chromatography

HRMS high resolution mass spectrometry

MeCN acetonitrile

MeOH methanol

MW microwave

NMR nuclear magnetic resonance r.t. room temperature

TFA trifluoroacetic acid

THF tetrahydrofuran

TLC thin-layer chromatography

The invention claimed is:

1. A compound of formula I,

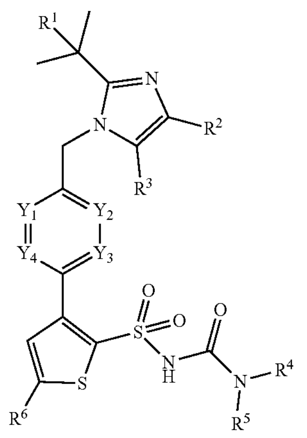

I wherein:

$R^1$ represents $C_{1-2}$ alkyl (optionally substituted by one or more fluorine atoms), $OR^7$ or a fluorine atom;

$R^2$ and $R^3$ each independently represent H or $C_{1-6}$ alkyl, optionally substituted by one or more halogen atoms;

$Y^1$, $Y^2$, $Y^3$ and $Y^4$ independently represent —CH—, —CF— or —N—;

$R^4$ represents;

(i) $C_{1-6}$ alkyl, $C_{1-6}$ alkoxy, or $C_{1-6}$ alkoxy-$C_{1-6}$ alkyl, the alkyl part of which are optionally substituted by one or more halogen atoms, or (ii) aryl, $C_{1-6}$ alkylaryl, $C_{1-3}$ alkenylaryl, heteroaryl, $C_{1-6}$ alkylheteroaryl or $C_{1-3}$ alkenylheteroaryl, each of which are optionally substituted by one or more substituents selected from halogen, —$CF_3$, $CF_3O$—, $C_{1-6}$ alkyl, and $C_{1-6}$ alkoxy;

$R^5$ represents H or $C_{1-6}$ alkyl, each of which is optionally substituted by one or more halogen atoms;

$R^6$ represents $C_{2-4}$ alkyl, optionally substituted by one or more halogens; and $R^7$ represents H or methyl, optionally substituted by one or more fluorine atoms, or a pharmaceutically-acceptable salt thereof.

2. A compound as claimed in claim 1, wherein $R^1$ represents $C_{1-2}$ alkyl, optionally substituted by up to three fluorine atoms, or $OR^7$.

3. A compound as claimed in claim 1, wherein $R^1$ represents methyl.

4. A compound as claimed in claim 1, wherein $R^2$ and $R^3$ both represent H.

5. A compound as claimed in claim 1, wherein $R^4$ represents $C_{1-4}$ alkyl or $C_{1-4}$ alkoxy-$C_{1-4}$ alkyl group, phenyl; $C_{1-3}$ alkylaryl; or $C_{1-3}$ alkylheteroaryl, each of which is optionally substituted by one or more halogen atoms.

6. A compound as claimed in claim 1, wherein $R^5$ represents H, methyl, ethyl, n-propyl, n-butyl or isobutyl.

7. A compound as claimed in claim 1, wherein $R^6$ represents n-propyl, n-butyl or isobutyl.

8. A compound as claimed in claim 1, wherein $R^7$ represents H or methyl.

9. A compound as claimed in claim 1, wherein $Y^1$ represents —CF— or —CH and $Y^2$, $Y^3$ and $Y^4$ all represent —CH—.

10. A compound as claimed in claim 1, which is:

furan-2-ylmethyl-3-[[5-isobutyl-3-[4-[(2-tert-butyl-imidazol-1-yl)methyl]phenyl]-2-thienyl]sulfonyl]urea, thiophen-2-ylmethyl-3-[[5-isobutyl-3-[4-[(2-tert-butyl-imidazol-1-yl)methyl]phenyl]-2-thienyl]sulfonylurea, 2-methoxyethyl-3-[[5-isobutyl-3-[4-[(2-tert-butyl-imidazol-1-yl)methyl]phenyl]-2-thienyl]sulfonylurea, pyridin-2-ylmethyl-3-[[5-isobutyl-3-[4-[(2-tert-butyl-imidazol-1-yl)methyl]phenyl]-2-thienyl]sulfonylurea, 1-[[3-[4-[(2-tert-butylimidazol-1-yl)methyl]-3-fluoro-phenyl]-5-isobutyl-2-thienyl]sulfonyl]-3-(2-pyridylmethyl)urea, 1-[[3-[4-[(2-tert-butylimidazol-1-yl)methyl]-3-fluoro-phenyl]-5-isobutyl-2-thienyl]sulfonyl]-3-ethyl-urea, or 1-[[3-[4-[(2-tert-butylimidazol-1-yl)methyl]-3-fluoro-phenyl]-5-isobutyl-2-thienyl]sulfonyl]-3-(2-thienylmethyl)urea.

11. A pharmaceutical formulation comprising a compound as defined in claim 1, or a pharmaceutically acceptable salt thereof in admixture with a pharmaceutically-acceptable, adjuvant, diluent or carrier.

12. A method of treatment of:

(i) an autoimmune disease selected from the group consisting of arthritis, rheumatoid arthritis, systemic sclerosis, systemic lupus erythematosus, multiple sclerosis, psoriasis and inflammatory bowel disease;

(ii) a viral respiratory tract infection and/or pneumonia as a consequence thereof;

(iii) a fibrotic disease;

(iv) a chronic kidney disease;

(v) pulmonary hypertension;

(vi) heart failure; and/or (vii) myocardial infarction;

which comprises administering an effective amount of a compound as defined in claim 1, or a pharmaceutically acceptable salt thereof, to a patient in need of such treatment.

13. A method of treatment as claimed in claim 12, wherein the disease is an interstitial lung disease.

14. A method of treatment as claimed in claim 13, wherein the interstitial lung disease is idiopathic pulmonary fibrosis or sarcoidosis.

15. A method of treatment as claimed in claim 12, wherein the autoimmune disease is rheumatoid arthritis or systemic sclerosis.

16. A method of treatment as claimed in claim 12, wherein the chronic kidney disease is diabetic nephropathy.

17. A method of treatment as claimed in claim 12, wherein the pulmonary hypertension is pulmonary arterial hypertension.

18. A method of treatment as claimed in claim 12, wherein the heart failure is with preserved ejection fraction.

19. A process for the preparation of a compound of formula I as defined in claim 1, which process comprises:

(i) reaction of a compound of formula II,

II

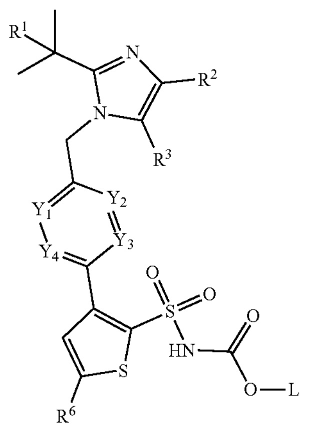

wherein $R^1$, $R^2$, $R^3$, $R^6$, $Y^1$, $Y^2$, $Y^3$ and $Y^4$ are as defined in claim 1 and L represents $C_{1-6}$ alkyl or aryl with a compound of formula III,

III $NHR^4R^5$ wherein $R^4$ and $R^5$ are as defined in claim 1;

(ii) for compounds of formula I in which $R^5$ represents H, reaction of a compound of formula IV,

IV

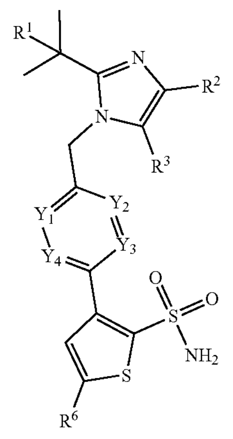

wherein $R^1$, $R^2$, $R^3$, $R^6$, $Y^1$, $Y^2$, $Y^3$ and $Y^4$ are as defined in claim 1, with a compound of formula V,

V

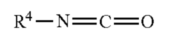

or a compound of formula VI,

VI

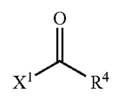

wherein $X^1$ is a suitable leaving group, and wherein, in each case, $R^4$ is as defined in claim 1.

20. A compound as claimed in claim 10, which is: pyridin-2-ylmethyl-3-[[5-isobutyl-3-[4-[(2-tert-butyl-imidazol-1-yl)methyl]phenyl]-2-thienyl]sulfonylurea.

* * * * *